United States Patent
Nakagawa et al.

(10) Patent No.: US 10,514,386 B2
(45) Date of Patent: Dec. 24, 2019

(54) SAMPLE LIQUID-SURFACE POSITION MEASUREMENT DEVICE AND SAMPLE LIQUID-SURFACE POSITION MEASUREMENT METHOD

(71) Applicant: HITACHI HIGH-TECHNOLOGIES CORPORATION, Minato-ku, Tokyo (JP)

(72) Inventors: Tatsuo Nakagawa, Tokyo (JP); Kiyotaka Sugiyama, Tokyo (JP); Tsukasa Suenari, Tokyo (JP); Iwao Suzuki, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 16/099,984

(22) PCT Filed: Apr. 11, 2017

(86) PCT No.: PCT/JP2017/014826
§ 371 (c)(1),
(2) Date: Nov. 8, 2018

(87) PCT Pub. No.: WO2017/203864
PCT Pub. Date: Nov. 30, 2017

(65) Prior Publication Data
US 2019/0128908 A1 May 2, 2019

(30) Foreign Application Priority Data
May 26, 2016 (JP) .................................. 2016-104926

(51) Int. Cl.
*G01N 35/00* (2006.01)
*G01N 33/49* (2006.01)
(Continued)

(52) U.S. Cl.
CPC ..... *G01N 35/00732* (2013.01); *G01F 23/292* (2013.01); *G01N 15/042* (2013.01);
(Continued)

(58) Field of Classification Search
CPC ................................................ G01N 35/00732
(Continued)

(56) References Cited

U.S. PATENT DOCUMENTS

3,891,324 A * 6/1975 Davies .................. B07C 5/3412
356/615
4,019,026 A * 4/1977 Nakanishi .......... G06K 7/10871
235/462.35
(Continued)

FOREIGN PATENT DOCUMENTS

JP     2004-037320 A    2/2004
JP     2004-037322 A    2/2004
(Continued)

OTHER PUBLICATIONS

Written Opinion for related International Application No. PCT/JP2017/014826, dated Jun. 13, 2017; 5 pages.
(Continued)

*Primary Examiner* — Tarifur R Chowdhury
*Assistant Examiner* — Omar H Nixon
(74) *Attorney, Agent, or Firm* — Procopio, Cory, Hargreaves & Savitch LLP

(57) ABSTRACT

A sample liquid-surface position measurement device includes: a first light source that illuminates a side face of a container containing a sample; a first optical measurement sensor that is located on the opposite side of the container from the first light source, and measures transmitted light from the first light source; a first label position measuring unit that measures a position of a label affixed to the container; and an analysis section that calculates a liquid- (Continued)

SIDE VIEW surface position or an interface position of the sample in the container, from transmitted-light intensity data in a longitudinal direction of the container which is measured by the first optical measurement sensor, and from the position of the label in the longitudinal direction of the container which is measured by the first label position measuring unit.

13 Claims, 21 Drawing Sheets

(51) Int. Cl.
    *G01F 23/292*     (2006.01)
    *G01N 15/04*     (2006.01)
    *G01N 15/05*     (2006.01)
    *G01N 35/10*     (2006.01)

(52) U.S. Cl.
    CPC ............. *G01N 15/05* (2013.01); *G01N 33/49* (2013.01); *G01N 2035/1025* (2013.01)

(58) Field of Classification Search
    USPC ........................................................ 356/614
    See application file for complete search history.

(56) References Cited

U.S. PATENT DOCUMENTS

| | | | |
|---|---|---|---|
| 4,074,130 A * | 2/1978 | Messman | B07C 5/3404 |
| | | | 198/374 |
| 4,282,431 A * | 8/1981 | Anthony, Jr. | G06K 7/10871 |
| | | | 235/462.36 |
| 6,161,759 A * | 12/2000 | Moss | G06K 7/10574 |
| | | | 235/462.01 |
| 2003/0141456 A1 | 7/2003 | McNeal et al. | |
| 2013/0118136 A1* | 5/2013 | Arima | B65C 3/065 |
| | | | 53/585 |
| 2014/0233042 A1 | 8/2014 | Klinec et al. | |
| 2016/0018427 A1 | 1/2016 | Streibl et al. | |

FOREIGN PATENT DOCUMENTS

| | | |
|---|---|---|
| JP | 2005-516212 A | 6/2005 |
| JP | 2006-010453 A | 1/2006 |
| JP | 2012-173226 A | 9/2012 |
| JP | 2014-163934 A | 9/2014 |

OTHER PUBLICATIONS

International Preliminary Report on Patentability for related International Application No. PCT/JP2017/014826, dated Nov. 15, 2017; 8 pages.

International Search Report for related International Application No. PCT/JP2017/014826, dated Jun. 13, 2017; English translation provided; 5 pages.

* cited by examiner

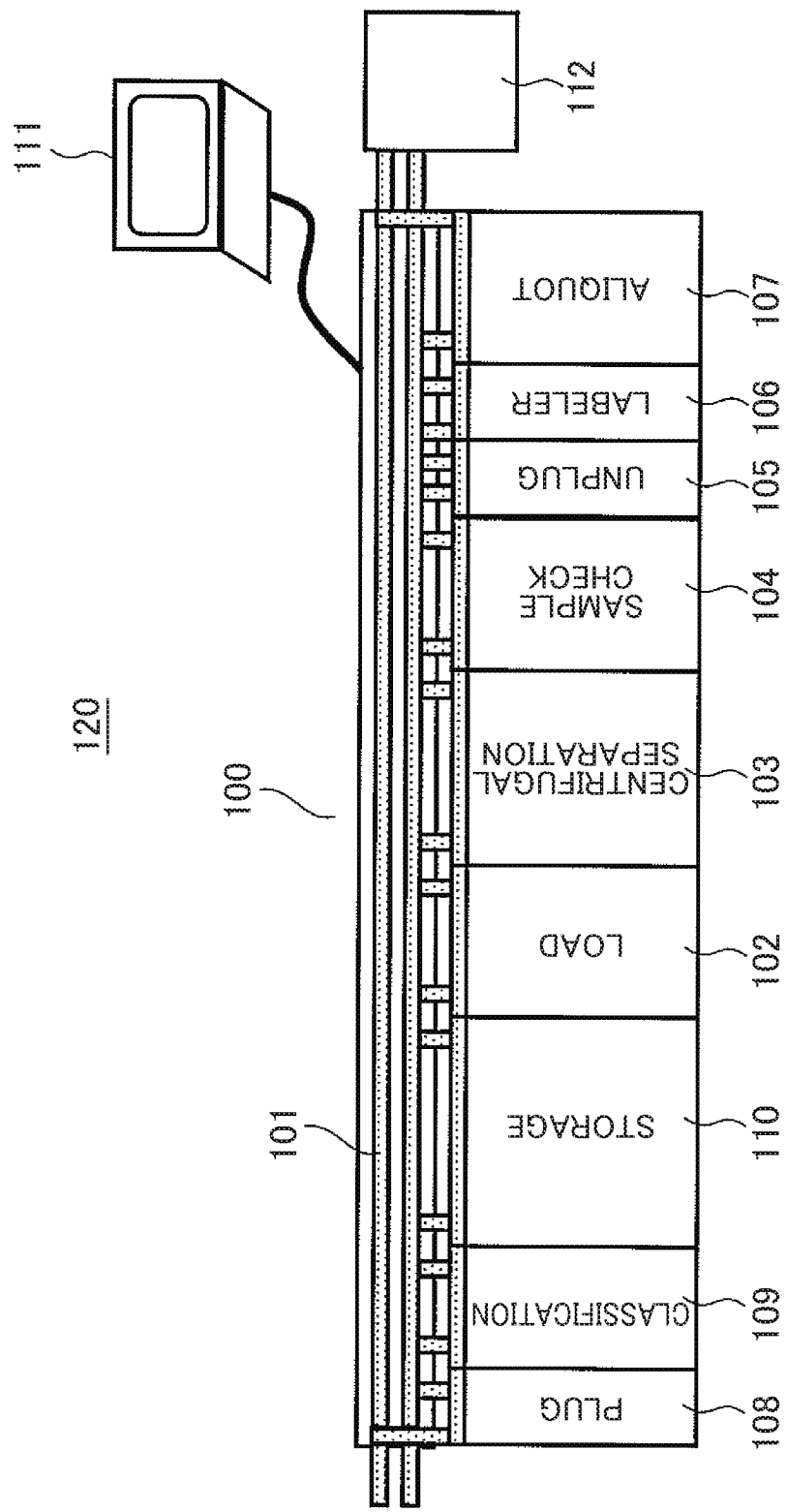

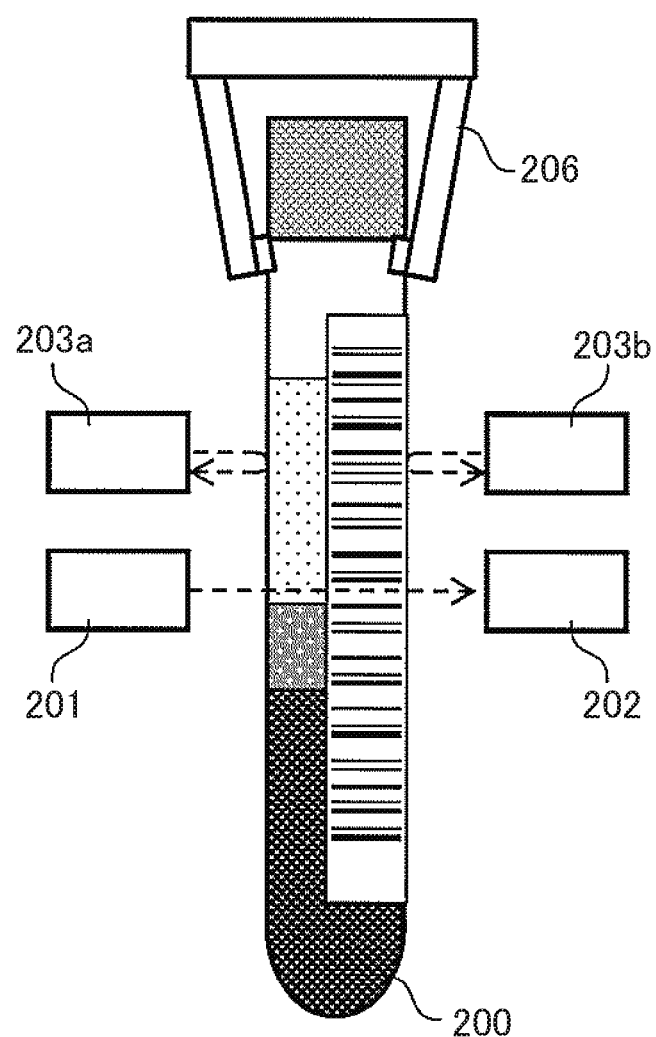

TOP VIEW

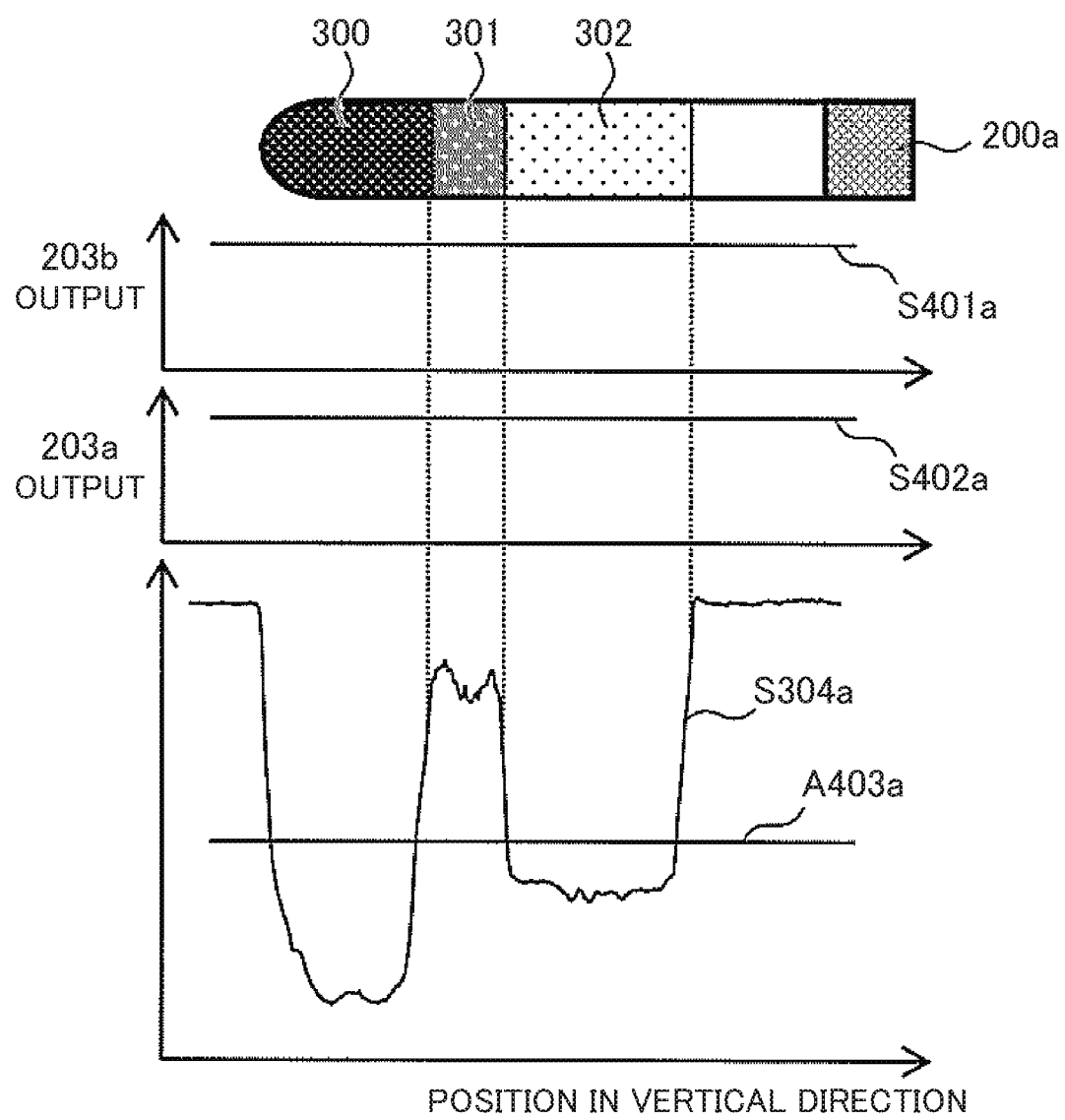

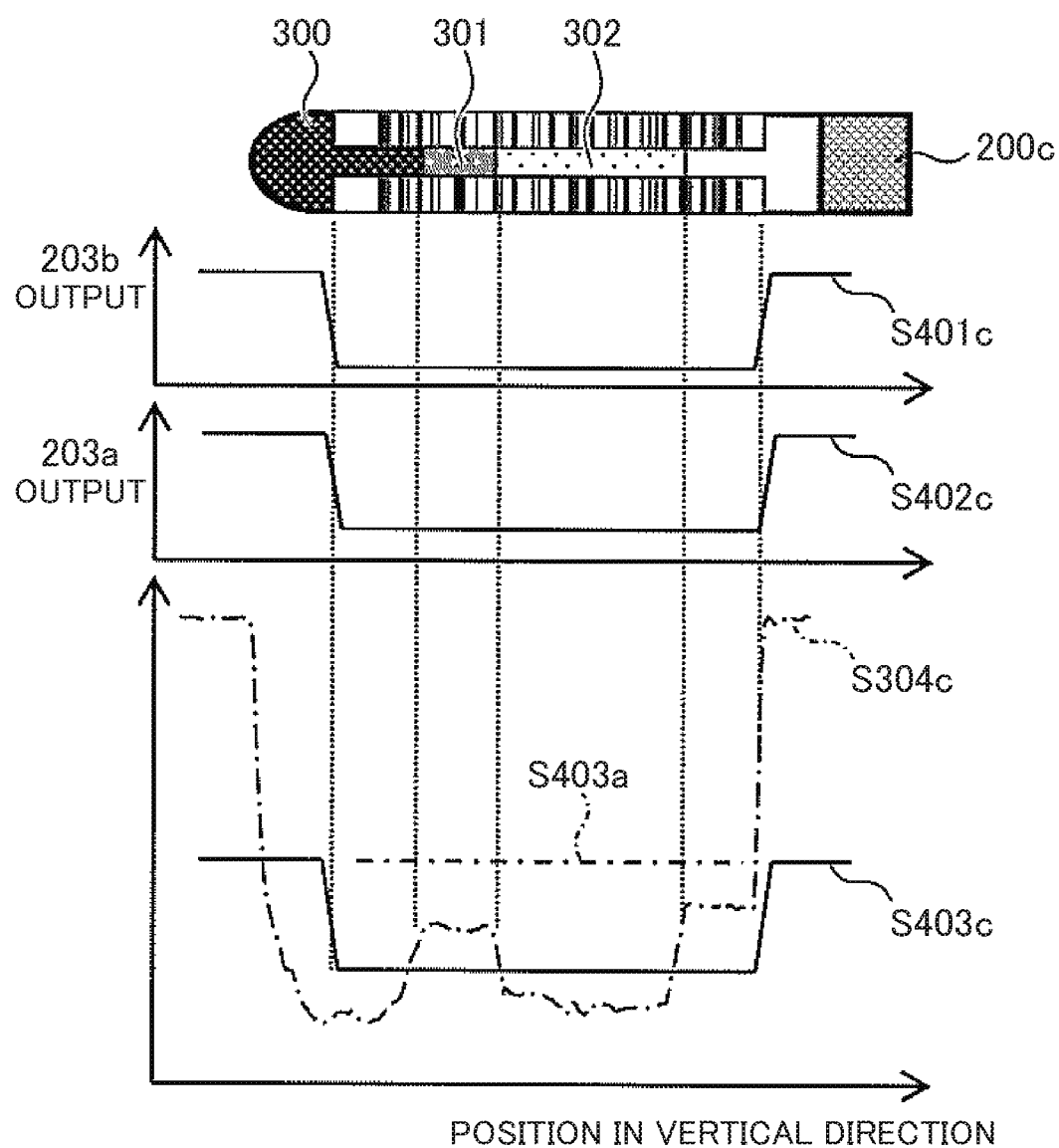

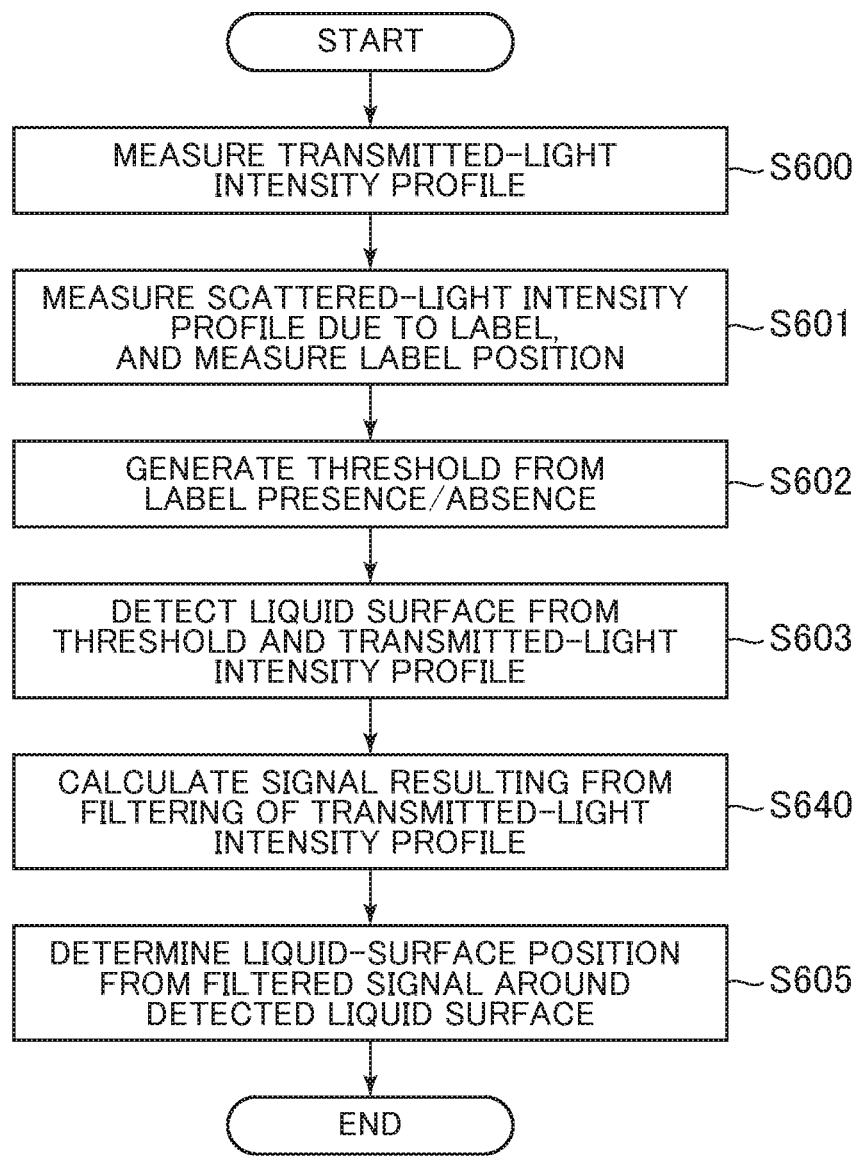

SIDE VIEW

TOP VIEW

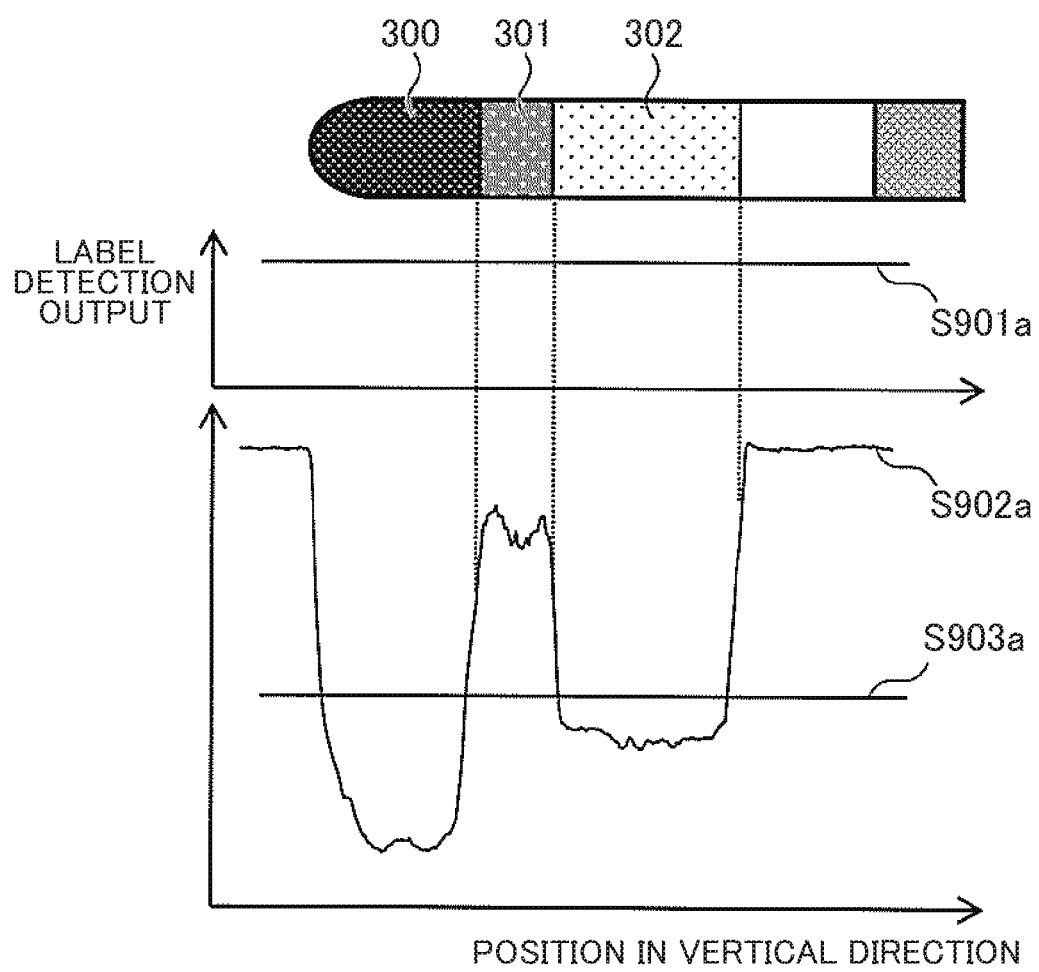

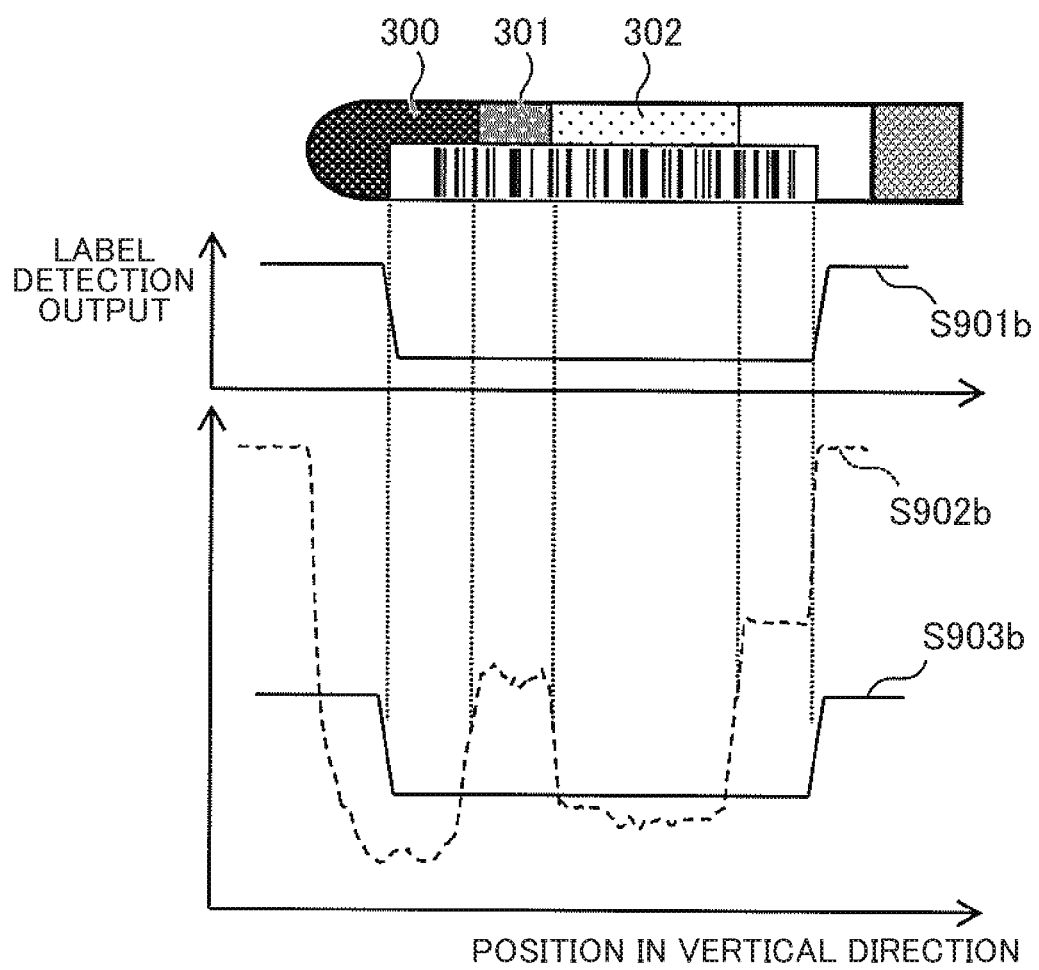

TOP VIEW

SAMPLE LIQUID-SURFACE POSITION MEASUREMENT DEVICE AND SAMPLE LIQUID-SURFACE POSITION MEASUREMENT METHOD

CROSS-REFERENCE TO RELATED APPLICATIONS

This application is a U.S. National Stage entry of PCT Application No: PCT/JP2017/014826 filed Apr. 11, 2017, which claims priority to Japanese Patent Application No. 2016-104926, filed May 26, 2016, the contents of which are incorporated herein by reference.

TECHNICAL FIELD

The invention relates to a device of measuring the position of the liquid surface of a sample and a method of measuring the position of the liquid surface of a sample.

BACKGROUND ART

Conventionally, techniques of using a biological sample to analyze components making up the biological sample have been provided. In the techniques, a dedicated container is prepared so that a biological sample taken from a patient is processed in the container. For example, where the sample is blood, the blood sampled is injected into a test tube with a separating agent pre-placed therein. Then, the test tube is subjected to centrifugation, so that the blood is separated into clot and serum in order to extract serum which is a component necessary for analysis.

Recently, inspection items that may be measured using serum has been diversified. As a result, the number of automatic analysis devices is increased, and thus an increase in number of samples is remarkable. Under the circumstances, there is an increasing need for systems for automatically processing (preprocessing) a biological sample before the biological sample is loaded into the automatic analysis device and/or for automatically transporting the sample to the automatic analysis device.

Examples of the pre-processes include a process to detect the amount of serum. If the amount of serum is uncertain, a probe may stick in the separating agent in the aliquot process to lead to a clogging error. If the amount of serum can be detected in the stage of preprocessing, then the probe height can be controlled to avoid the clogging error. Further, if the amount of serum is less than the amount required for analysis, analysis items are provided with priorities to determine an aliquot amount. Thus, if the amount of serum is able to be detected in the state of preprocessing, the enhanced efficiency of the measurement test using serum may be expected.

As a technique to detect the amount of serum or a technique to measure the position of liquid surface of a sample such as serum or the like, Patent Literature 1 discloses the interface-position determining method that uses a first light beam which passes through serum but is blocked by clot and a second light beam which is blocked by both serum and clot to detect the light resulting from the first and second beams being transmitted through the container. Further, Patent Literature 2 discloses the configuration that uses a line sensor to detect the transmitted light from the infrared surface light source to identify the serum interface position. Also, Patent Literature 3 discloses the configuration that uses derivative value data to detect the liquid surface position.

CITATION LIST

Patent Literature

Patent Literature 1: Japanese Unexamined Patent Application Publication (Translation of PCT Application) No. 2005-516212
Patent Literature 2: Japanese Unexamined Patent Application Publication No. 2004-37320
Patent Literature 3: Japanese Unexamined Patent Application Publication No. 2004-037322

SUMMARY OF INVENTION

Technical Problem

A label affixed to the container surface must be taken into account for measurement of the position of the liquid surface of a biological sample such as serum or the like in a container such as a test tube or the like without removing the lid. Examples of labels include a prelabel with its kind, a lot number and/or the like printed thereon, a label bearing each patient ID for sample identification and/or the like in barcode form or the like, and the like. Because of this, a plurality of labels may be affixed to a single container.

Patent Literature 2 discloses a liquid-surface position determining method that uses a means for detecting the label position (a gloss sensor) to find a label gap and then rotates a line sensor to be pointed at the gap and then to perform measurement in a label-absent range. However, in conditions where a plurality of labels is affixed, there may not be such a label gap. Therefore, there is a need for a method by which a liquid surface can be detected even if a label or labels is affixed to the entire perimeter of the container without any gap. Further, when measurement is performed by allowing light to pass through a plurality of labels, the light incident on the label(s) is reflected or scattered. Because of this, the transmitted light intensity is low, making the measurement difficult. Even in such cases, high reliable detection of liquid surface position is needed.

Also, Patent Literature 3 discloses the configuration in which a derivative value of the transmitted light intensity is calculated and the liquid surface position is detected based on the differential properties at the liquid surface. However, in conditions where a plurality of labels is affixed, the transmitted light intensity is low. Therefore, using only the derivative value of the transmitted light intensity cannot easily provide high reliable detection of a very small amount of features such as coming from liquid surface meniscus.

Accordingly, the present invention has been made to address the above problems and an object thereof is to provide a technique to achieve high-accuracy detection of the liquid-surface or interface position of a sample in a labeled container.

Solution to Problem

For example, the configuration set forth in the claims is employed to address the above problems. The present application includes a plurality of solutions to the above problems, and in one example, a sample liquid-surface position measurement device is provided, which includes: a first light source that illuminates a side face of a container containing a sample; a first optical measurement sensor that is located on the opposite side of the container from the first light source, and measures transmitted light from the first light source; a first label position measuring unit that measures a position of a label affixed to the container; and an analysis section that calculates a liquid-surface position or an interface position of the sample in the container, from transmitted-light intensity data in a longitudinal direction of the container which is measured by the first optical measurement sensor, and from the position of the label in the longitudinal direction of the container which is measured by the first label position measuring unit.

Further, in another example, a method of measuring a position of a liquid surface of a sample is provided, which includes: causing a first light source to illuminate aside face of a container containing a sample; causing a first optical measurement sensor, which is placed on the opposite side of the first light source with the container therebetween, to measure transmitted light passing from the first light source; a causing a first label position measuring unit to measure a position of a label affixed to the container; and a causing an analysis section to calculate a liquid-surface position or an interface position of the sample in the container, based on transmitted-light intensity data in a longitudinal direction of the container which is measured by the first optical measurement sensor, and the position of the label in the longitudinal direction of the container which is measured by the first label position measuring unit.

Advantageous Effects of Invention

According to the present invention, the liquid surface or interface position of a sample in a labeled container is able to be detected with high accuracy. Further features in connection to the present invention will be apparent from the description of the specification and the accompanying drawings. Also, the above and other problems, configurations, effects will be made apparent from the following description of embodiments.

BRIEF DESCRIPTION OF DRAWINGS

FIG. 1 is a block diagram illustrating the overall configuration of a biological sample analysis device in accordance with a first embodiment.

FIG. 2A is a side view of a liquid-surface position measurement device in accordance with the first embodiment.

FIG. 4A is a first example of a transmitted-light intensity profile measured by the liquid-surface position measurement device, output from a label position measuring unit, and thresholds, in accordance with the first embodiment.

FIG. 4C is a third example of a transmitted-light intensity profile measured by the liquid-surface position measurement device, output from a label position measuring unit, and thresholds, in accordance with the first embodiment.

FIG. 6 is an operation flow to measure the liquid surface position at the liquid-surface position measurement device in accordance with the first embodiment.

FIG. 9A is a first example of a transmitted-light intensity profile measured by the liquid-surface position measurement device, output from a label position measuring unit, and thresholds, in accordance with the second embodiment.

FIG. 9B is a second example of a transmitted-light intensity profile measured by the liquid-surface position measurement device, output from a label position measuring unit, and thresholds, in accordance with the second embodiment.

DESCRIPTION OF EMBODIMENTS

Figure 2B:
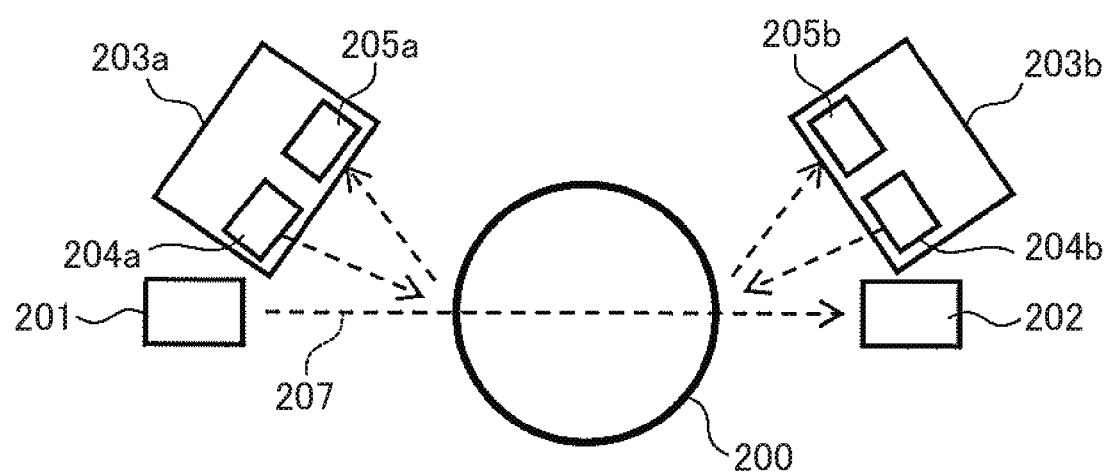
FIG. 2B is a top view of the liquid-surface position measurement device in accordance with the first embodiment.

Embodiments in accordance with the present invention will now be described with reference to the accompanying drawings. The accompanying drawings illustrate specific embodiments in accordance with the principles of the present invention, which are provided for the purpose of understanding the present invention and therefore should not be interpreted as limiting the present invention. It should be noted that, throughout all the drawings for describing embodiments and embodiments, like reference signals are used to designate elements having like functions, and a repetitive description is omitted.

The following embodiments relate to a device for detecting the liquid-surface position of a sample and a method for detecting the liquid-surface position of a sample and, more particularly, to a sample preprocessing device used for a biological sample made up of a plurality of components to detect the component interface or liquid-surface position or the amount of sample. In examples described below, a sample is placed in a test tube, but a sample is not limited to be placed in a test tube and another container may be used.

First Embodiment

A biological sample analysis device in accordance with a first embodiment will be described with reference to FIG. 1 to FIG. 6. FIG. 1 is a block diagram illustrating the overall configuration of the biological sample analysis device in accordance with the first embodiment.

A biological sample automatic analysis device is a device for preprocessing a biological sample (e.g., blood) taken from a patient and analyzing the preprocessed biological sample. The biological sample analysis device 120 includes: a preprocessing system 100; a control PC 111 that controls the entire preprocessing system 100; and an automatic analyzer 112 that is connected to the preprocessing system 100 and analyzes a component or components of the biological sample.

The preprocessing system 100 is made up of a plurality of modules. The preprocessing system 100 includes, as basic elements, a transport line 101, a load module 102, a centrifugal separation module 103, a sample check module (detection device) 104, a unplug module 105, a labeler 106, an aliquot module 107, a plug module 108, a classification module 109, and a storage module 110.

The load module 102 is a module in which a sample (a test tube with blood inside) is loaded. The centrifugal separation module 103 is a module for performing centrifugation on the loaded sample. The sample check module 104 is a module detecting information about serum (such as a serum index, the amount of serum and/or the like). The unplug module 105 is a module opening the lid of the sample after centrifugation. The aliquot module 107 is a module subdividing (aliquoting) the sample after centrifugation for analysis in the automatic analyzer 112 and/or the like, and the labeler 106 is a module affixing barcode to a container for the subdivision. The plug module 108 is a module closing the lid of the sample. The storage module 110 is a module storing the sample lidded. The classification module 109 is a module classifying the aliquoted sample container. The transport line 101 has a performs transportation of the sample from one module to another.

The following is a sample analysis flow. First, a test tube is used to take blood from a patient (whole blood). The test tube is loaded in the load module 102 of the preprocessing system 100. Note that taking blood and loading are performed manually by the user, and the subsequent operations are automated operations by the preprocessing system 100. Note that generally the taking blood is performed by a nursing staff and the loading is performed by a laboratory technician. The taking blood may be performed in a facility different from the facility in which the biological sample analysis device 120 is installed.

The loaded test tube is transported to the centrifugal separation module 103 by the transport line 101 to be subjected to centrifugation. A separating agent is preplaced in the test tube, and therefore, through the centrifugation, the sample is separated into a clot layer with a relatively high specific gravity and a serum layer with a relatively low specific gravity. The sample after centrifugation is transported to the sample check module 104 by the transport line 101 to detect serum index and the amount of serum. The method of detecting the liquid-surface position in the sample check module 104 will be described in detail later.

The sample of which the serum index is determined to be hemolytic, jaundiced or chylous is delivered to the classification module 109 by the transport line 101, which is then classified as an error sample. On the other hand, the sample of which the serum index is normal and also the amount of serum is detected is delivered to the unplug module 105 by the transport line 101. In the unplug module 105, the lid of the sample after centrifugation is removed, and the unlidded sample is delivered to the aliquot module 107 by the transport line 101. At the same time, a subdivision container affixed with barcode at the labeler 106 is also delivered to the aliquot module 107. The aliquot module 107 dispenses the serum into a subdivision container on the basis of the information about the serum detected by the sample check module 104. The sample after the completion of aliquoting is transported to the plug module 108 by the transport line 101. In the plug 108 the lid of the sample is closed, and then the lidded sample is stored in the storage module 110. The subdivision container stored is transported to the automatic analyzer 112 for analysis of various components.

FIG. 2A and FIG. 2B are configuration diagrams of a device of measuring the liquid-surface position. The liquid-surface position measurement device includes a light source 201, an optical measurement sensor 202, first and second label position measuring units 203a, 203b, and a test tube grasping unit 206. The light source 201 and the optical measurement sensor 202 are arranged to sandwich the test tube 200. The light source 201 illuminates the side of the test tube 200 containing a sample which is subject to a liquid-surface position measurement. The optical measurement sensor 202 is located on the opposite side of the light source 201 with the test tube 200 therebetween, and measures the light that is emitted from the light source 201 and then passes through the test tube 200.

Since the first and second label position measuring units 203a, 203b are identical in configuration, the first label position measuring unit 203a is described in below and a description of the second label position measuring unit 203b is omitted. The first label position measuring unit 203a measures, in the longitudinal direction of the test tube 200, the position of a label affixed to the test tube 200. The first label position measuring unit 203a includes a light source 204a and an optical measurement sensor 205a. The light emitted from the light source 204a is reflected and scattered by the surface of the test tube 200. The light measurement sensor 205a receives a portion of the reflected light or the scattered light resulting from impinging of the light from the light source 204a on the test tube 200.

When comparisons are made of a test tube 200 labeled on the wall surface with an unlabeled test tube 200, there is a difference in the reflected light and the scattered light from the wall surface of the test tube 200. Specifically, for example, in an area where a label is affixed, the label causes the light to be scattered. Because of this, the amount of light received by the optical measurement sensor 205a increases. On the other hand, in an area where a label is not affixed, because the light enters the surface of the transparent test tube 200, the amount of scattered light decreases as compared with the case of the label existing. Therefore, the amount of light received by the optical measurement sensor 205a decreases. For example, the liquid-surface position measurement device determines the position where the scattered light intensity becomes below a predetermined threshold, as a position where a label exists. In this manner, since the scattered light changes depending on the presence or absence of a label, the presence or absence of a label can be detected by measuring the scattered light.

It should be noted that the presence or absence of a label may be detected by measuring the reflected light instead of the scattered light, or the like. In a further example, the optical measurement sensor 205a may be configured to be placed on the optical axis direction of the light emitted from the light source 204a (e.g., on the opposite side with respect to the test tube 200) to receive the light from the light source 204a.

The light source 204a emits light toward near the wall surface of the test tube 200 on the optical axis (optical path) 207 between the light source 201 and the optical measurement sensor 202. In other words, the light source 204a emits light to impinge on the intersection of the test tube 200 and the optical axis 207 of the light from the light source 201. By doing this, it is possible to detect the presence/absence of a label on the optical axis 207 between the light source 201 and the optical measurement sensor 202. On the optical axis 207 between the light source 201 and the optical measurement sensor 202, the wall surface of the test tube 200 is located in two places, the place where the light travels from the light source 201 into the test tube 200 and the place where the light exits the test tube 200. Therefore, the light received by the optical measurement sensor 202 is affected by the label affixed on the two places. The first and second label position measuring units 203a, 203b are arranged respectively to detect the presence/absence of label in the two places. The first label position measuring unit 203a is placed on the side of the light source 201, and thus measures the position of the label in a position where the light from the light source 201 enters the test tube 200. On the other hand, the second label position measuring unit 203b is placed on the side of optical measurement sensor 202, and thus measures the position of the label in a position where the light from the light source 201 passes through and emerges from the test tube 200. With this configuration, scattering and attenuation of the light can be estimated at the position where the light enters the test tube 200 and the position where the light emerges from the test tube 200.

As a wavelength of the light sources 201, a wavelength absorbed by clot and serum is employed. For example, a wavelength in a range from 1400 nm to 1600 nm in the near-infrared region or a wavelength in a range around 1900 nm is selected as a wavelength of the light source 201. Because light of the wavelength described above is absorbed by water, the light is absorbed by serum consisting largely of water. More specifically, a wavelength in a range from 1450 nm to 1550 nm may be used as a wavelength of the light source 201. For the light source 201, a laser may be used or a light-emitting diode may be used. Using the laser provides high directivity and high output. On the other hand, the light-emitting diode is inferior in directivity and output power as compared with the laser, but has the advantage of low costs.

Figure 3A:
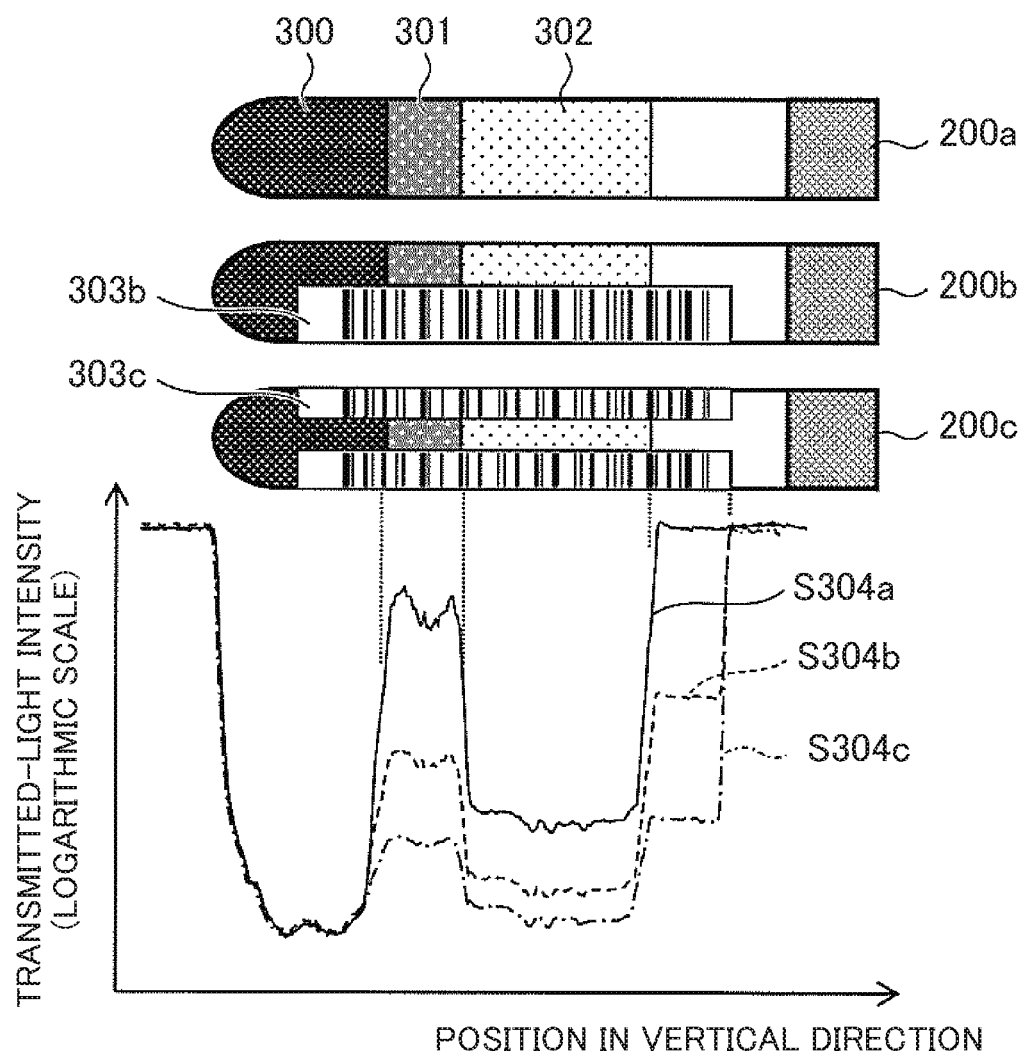
FIG. 3A is an example transmitted-light intensity profile measured by the liquid-surface position measurement device in accordance with the first embodiment.

FIG. 3A is a schematic diagram illustrating the amount of light received by the optical measurement sensor 202 when the light is emitted from the light source 201 and then passes through the test tube 200. A test tube 200a is an unlabeled test tube. A test tube 200b is a test tube with a label 303a placed only on one side. A test tube 200c is a test tube with a label 303c placed on both sides.

FIG. 3A is an example of data (logarithmic scale) on transmitted light intensities measured along the vertical direction for each of the test tubes 200a, 200b, 200c. S304a shows the transmitted light intensity data (hereinafter referred to as "transmitted light intensity profile) for the test tube 200a. S304b shows the transmitted light intensity profile for the test tube 200b. S304c shows the transmitted light intensity profile for the test tube 200c.

The blood sample after centrifugation is separated into a clot 300, a separating agent 301, and a serum 302 in this order from the bottom of the test tube. Because a portion corresponding to the clot 300 is impenetrable to light, most of light is not passed regardless of the number of affixed labels. On the other hand, the separating agent 301 is composed of a polyolefin based resin and/or the like, and has properties of attenuating near-infrared light but allowing light to pass.

If the label 303b, 303c is affixed, the transmitted light intensity is reduced under the influence of the scattering, reflection and attenuation on the label 303b, 303c. Further, the light from the light source 201 is absorbed by the portion corresponding to the serum 302. However, rather than being fully absorbed by the serum 302, the light partially passes to be received by the optical measurement sensor 202. Therefore, the transmitted light intensity changes depending on the number of labels. For example, the transmitted light intensity in the portion corresponding to the serum 302 is highest in the test tube 200a, second highest in the test tube 200b and lowest in the test tube 200c.

Also, in a position above the serum 302 (an empty portion of the test tube), the transmitted light intensity changes depending on the number of labels because the light is reflected, scattered and attenuated by the label 303b, 303c.

Figure 3B:
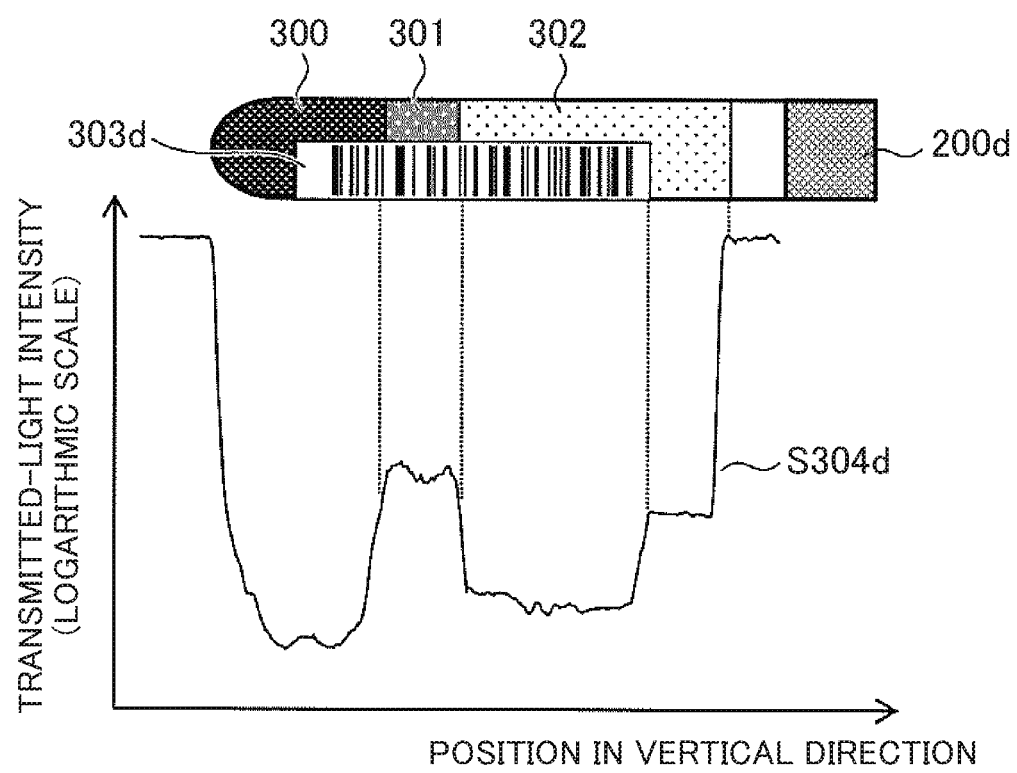
FIG. 3B is another example transmitted-light intensity profile measured by the liquid-surface position measurement device in accordance with the first embodiment.

FIG. 3B is another example of the amount of light received by the optical measurement sensor 202 when the light is emitted from the light source 201 and then passes through the test tube 200. FIG. 3B illustrates the transmitted light intensity on a test tube 200d. As compared with the example in FIG. 3A, FIG. 3B differs in the relationship between the position of the top surface of the sample serum 302 and the position of the top end of the label 303d, in which the position of the top surface of the serum 302 is located above the top end of the label 303d.

A labeled region and an unlabeled region exist on the side face of the test tube 200d as a region where the serum 302 exists. Therefore, even in the same serum 302 region, the transmitted light intensity greatly changes depending on the presence/absence of the label. In comparison of the test tube 200d in FIG. 3B with the test tube 200b (labeled on only one side) in FIG. 3A, even though the positional relationship between the top surface of the serum 302 and the top end of the label is reversed, the transmitted light intensity profiles are similar. In such a transmitted light intensity profile, it is difficult to distinguish whether the top surface of the serum 302 or the top end of the label.

Figure 4B:
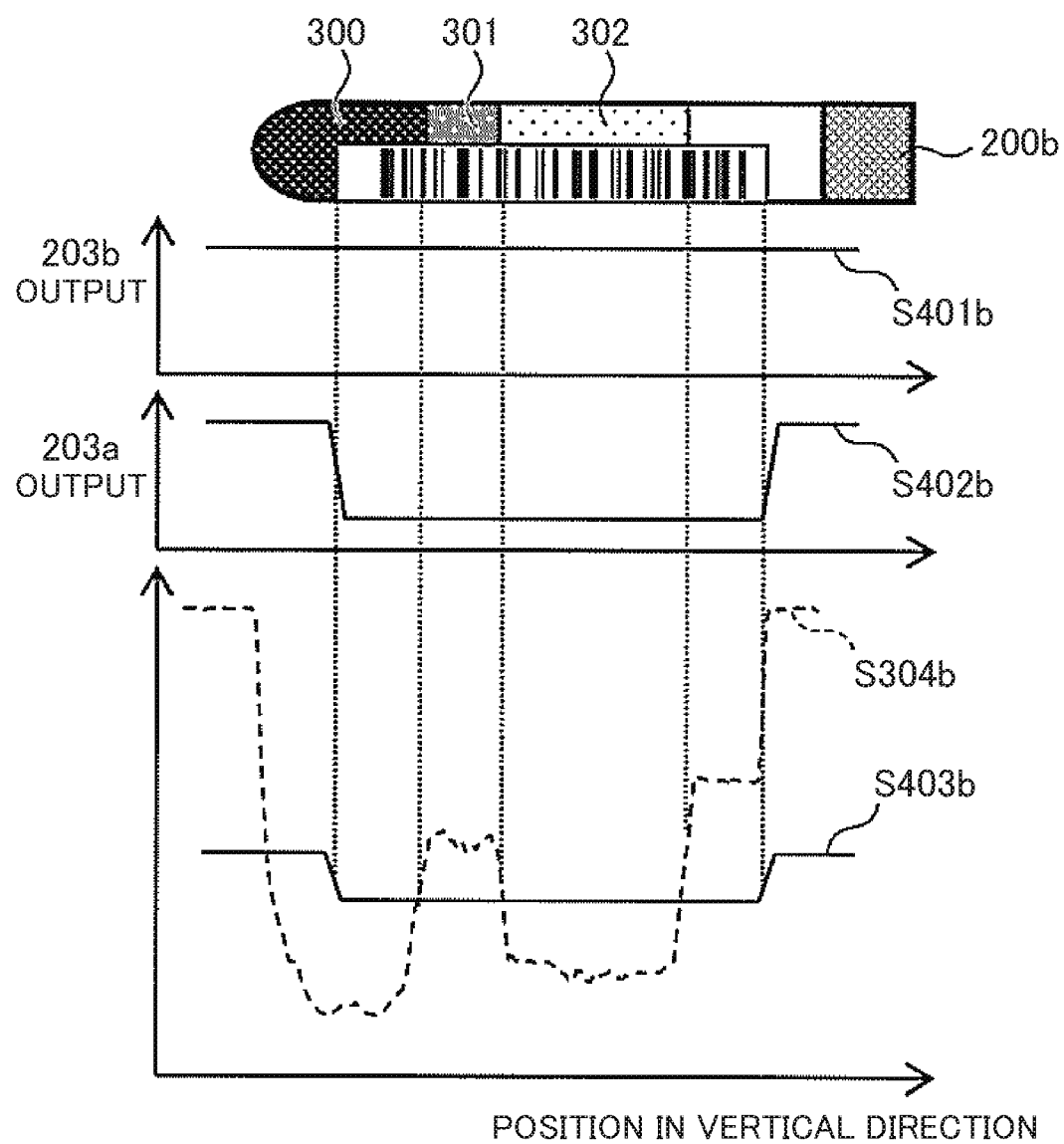
FIG. 4B is a second example of a transmitted-light intensity profile measured by the liquid-surface position measurement device, output from a label position measuring unit, and thresholds, in accordance with the first embodiment.

FIG. 4A to FIG. 4C are schematic diagrams illustrating the output of the label position measuring unit 203 in addition to the intensity profile of the transmitted light received by the optical measurement sensor 202. Note that the output of each of the first and second label position measuring units 203a, 203b is shown as Lo level when the label is detected and as Hi level when no label is detected.

FIG. 4A is an example of the unlabeled test tube 200a. Where a label is not affixed, both the outputs S401a, S402a of the first and second label position measuring unit 203a, 203b are Hi level. Accordingly, the liquid-surface position measurement device (more specifically, a data analysis section 705 described later) compares the transmitted light intensity profile S304a with a threshold S403a for the case of no label existing, and detects the liquid surface or interface position from the intersection between the transmitted light intensity profile S304a and the threshold S403a. Specifically, the liquid-surface position measurement device detects the boundary surface between the separating agent 301 and the serum 302 and the boundary surface between the serum 302 and the air (vacuum portion if a vacuum test tube is used) layer above the serum 302. Similarly, the liquid-surface position measurement device can also detect the boundary surface between the clot 300 and the separating agent 301.

FIG. 4B is an example of the test tube 200b labeled on only one side. When a label is affixed to one side, the output S402b of the first label position measuring unit 203a located on one side becomes Lo level in a labeled range. On the other hand, the output S401b of the second label position measuring unit 203b becomes Hi level. In the labeled area, the light from the light source 201 is reflected, scattered and attenuated. Because of this, the intensity of the transmitted light received at the optical measurement sensor 202 is reduced. Therefore, a relatively low threshold S403b is set in the labeled range as compared with the case of no label affixed. The liquid-surface position measurement device compares between the transmitted light intensity profile S304b and the threshold S403b and thus detects the liquid-surface or interface position from the intersection of the transmitted light intensity profile S304b and the threshold S403b.

FIG. 4C is an example of the test tube 200c labeled on both sides. Outputs S401c, S402c of the first and second label position measuring unit 203a, 203b both becomes Lo level in a labeled range. Therefore, a lower threshold S403c is set in this range as compared with the case of a label affixed on only one side. The liquid-surface position measurement device compares between the transmitted light intensity profile S304c and the threshold S403c and thus detects the liquid-surface or interface position from the intersection of the transmitted light intensity profile S304c and the threshold S403c.

FIG. 4C illustrates a threshold S403a for the case of no label existing, for reference purposes. In the case of using the threshold S403a, because of a low intensity of transmitted light in the portion corresponding to the separating agent 301, distinctions among the separating agent 301, the clot 300 and the serum 302 is not able to be made, so that the interface of the serum 302 and the separating agent 301 cannot be detected. Further, because the transmitted light intensity is low in a label portion above the serum 302, the top surface of the serum 302 cannot be detected, resulting in the top end of the label being incorrectly detected as the top surface of the serum. On the other hand, detecting the label presence/absence and changing the threshold in the labeled portion enables the detection of the top surface of the serum 302 and the top surface of the separating agent 301 in which the transmitted light intensity becomes low.

In this manner, the liquid-surface position measurement device uses the first and second label position measuring units 203a, 203b to detect the label presence/absence, and changes the threshold (threshold for detecting each interface in a sample) based on the detection result. For example, the larger the number of labels detected, the lower the threshold becomes. In the examples in the FIG. 4A to FIG. 4C, the magnitude relationship between thresholds in the positions where the label is detected is S403a>S403b>S403c. The liquid-surface measurement device uses the threshold in accordance with the label detection result in order to detect the interface (at least one of the interface between the clot 300 and the separating agent 301, the interface between the separating agent 301 and the serum 302 and the top liquid-surface of the serum 302) within the sample.

Because the output of the single label position measuring unit can take two values (Hi, Lo), the combination or patterns of the outputs of the two label position measuring units 203a, 203b may be four.

Therefore, the liquid-surface position measurement device may define thresholds respectively corresponding to the four patterns. The thresholds determined here are for eliminating the influences of reflection, attenuation and scattering on the label to the intensity of the transmitted light from the light source 201 to the optical measurement sensor 202. By doing this, even if the transmitted light intensity is reduced by an affixed label, the detection of the liquid surface is enabled without false detection.

Note that the configuration in which a lower threshold is set for the labeled portion has been described in the embodiment, but this is not intended to be limiting. The threshold may be fixed, and the liquid-surface position measurement device may perform processing for increasing the transmitted light intensity profile only in the labeled portion in order to detect the liquid surface. This corresponds to a liquid-surface detection performed by compensating for transmitted light intensity attenuated by the label so that a state similar to the unlabeled state is produced equivalently.

Further, the polarity of the output of the label position measuring unit 203a, 203b may be reversed. Specifically, the label position measuring unit 203a, 203b may output Hi level if the label exists, and output Lo level if no label exists. Also, the configuration of the label position measuring unit 203a, 203b outputting Hi level or Lo level in digital value has been described, but this is not intended to be limiting. By using a sensor outputting analog values, the label position measuring unit 203a, 203b may determine based on the analog values whether a label is present or absent, and/or the threshold may be defined as an analog value.

For the light source 204a, 204b of the label position measuring unit 203a, 203b, for example, a red light-emitting diode is used. Using visible wavelength light facilitates adjustment to align the illumination point with the optical axis 207 between the light source 201 and the optical measurement sensor 202, and/or the like. Also, the light source of red visible light has an advantage of low costs as compared with use of near-infrared light and ultraviolet light.

If the light source 204a, 204b of the label position measuring unit 203a, 203b illuminates the test tube 200 from directly opposite the test tube 200, then the directly reflected light is input to the optical measurement sensor 205a, 205b of the label position measuring unit 203a, 203b, which may make it difficult to detect the label presence/absence. In such cases, the light from the light source 204a, 204b of the label position measuring unit 203a, 203b may be slightly inclined with respect to the test tube 200 to prevent the reflected light from being reflected directly toward the label position measuring unit 203a, 203b. Specifically, the light source 204a, 204b preferably illuminates at an inclination of from about 5 degrees to about 40 degrees with respect to the optical axis 207 so that the light scattered by the surface of the test tube 200 is received at the optical measurement sensor 205a, 205b. Because the scattered light varies depending on the label presence/absence, the label presence/absence can be detected robustly by measuring the scattered light rather than measuring the reflected light.

Further, the label is printed with barcode and/or the like. If a printed black line is thick or the like, the scattered light is decreased as compared with a white portion of the label, thus raising the possibility of making a false determination that there is no label even though the label exits. This can be avoided by increasing the spot diameter of the optical measurement sensor 205a, 205b to be wider than the printed line. Also, by taking a moving-average of the outputs of the optical measurement sensor 205a, 205b, small influences of printing in the label can be eliminated to achieve accurate measurement of the label presence/absence.

Further, the positional relationship between the two label position measuring units 203a, 203b is not limited to the arrangement illustrated in the figures. For example, if light of the same wavelength is used in the two label position measuring units 203a, 203b, interference may occur and thus a malfunction may possibly occur. In such cases, an arrangement that prevents occurrence of interference is preferably provided by, for example, locating the label position measuring units 203a, 203b away from each other in the vertical direction. Also, the positional relationship between the label position measuring units 203a, 203b, and the light source 201 and optical measurement sensor 202 in the vertical direction is not limited to the arrangement illustrated in the figures. The label position measuring units 203a, 203b may be located above the light source 201 and the optical measurement sensor 202.

An optical measurement sensor with a wide dynamic range is required to support the detection of the liquid surface in the test tube to which a plurality of labels is affixed. Specifically, for example, the configuration in which the output current of a photodiode is converted to a voltage, which then is amplified by a logarithmic amplifier, is conceivable. For the photodiode, for example, a sensor with sensitivity to near-infrared light which is made out of InGaAs (indium gallium arsenide) may be used. By using the logarithmic amplifier, the amplification factor for weak light can be increased and the amplification for strong light can be compressed. This enables the detection of light with a wide dynamic range. And, an AGC (Automatic Gate Control) amplifier may be used. The AGC amplifier dynamically changes gain. Thereby, a wide dynamic range can be provided and reception of from low-power light to high-power light can be achieved. And, the light source may be caused to produce pulse light emission, which may be synchronized for measurement (synchronization detection), in order to improve the signal-to-noise ratio.

A method for further higher accuracy of the liquid-surface position in the embodiment will be described with reference to FIG. 5A to FIG. 5C.

In the embodiment, the label affixed to the test tube is detected by measurement from external. Therefore, it is impossible to make discrimination between a label overlapping state and a label non-overlapping state. FIG. 5A is a first example where two labels are affixed to the test tube 200. In the case of this example, the light from the light source 201 passes through two layers plus two layers, total four layers, of the labels. Also, FIG. 5B is a second example where two labels are affixed to the test tube 200. In the case of this example, the light from the light source 201 passes through one layer plus one layer, total two layers of the labels. In this manner, even in the same situation where two labels are affixed to the test tube 200, there are two cases where the light from the light source 201 passes through the overlapping portions of the labels and passes through the non-overlapping portions of the labels. The attenuation of the transmitted light is greater when light passes through four layers.

Figure 5A:
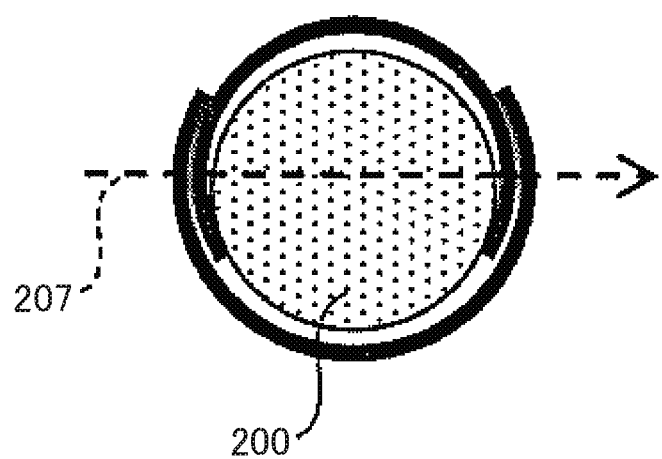
FIG. 5A is an example where four layers of labels exit on an optical axis of the liquid-surface position measurement device.
Figure 5B:
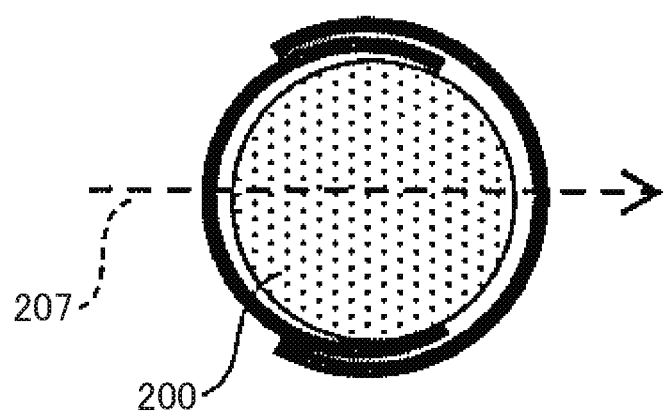
FIG. 5B is an example where two layers of labels exit on an optical axis of the liquid-surface position measurement device.
Figure 5C:
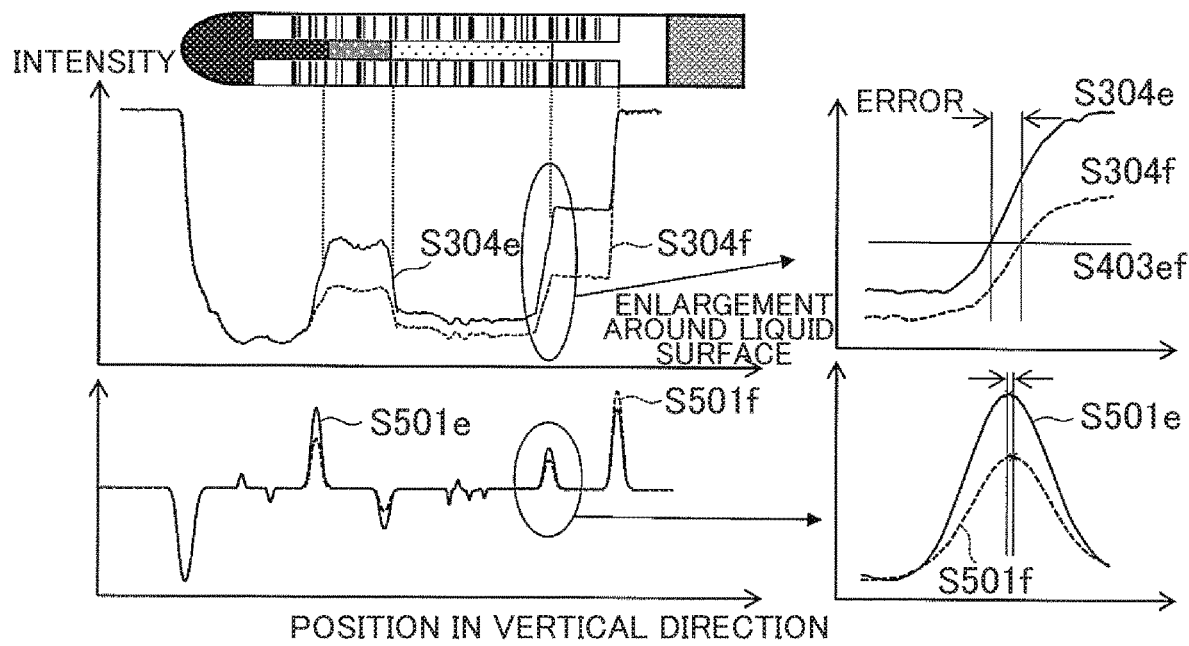
FIG. 5C is an example of a filtered signal and a transmitted-light intensity profile in the cases of FIG. 5A and FIG. 5B.

FIG. 5C is an example of the transmitted light intensity profile and a signal after passing through a filter in the cases of FIG. 5A and FIG. 5B. Reference sign S304e denotes the transmitted light intensity profile in the case of FIG. 5B, while reference sign S304f denotes the transmitted light intensity profile in the case of FIG. 5A. Note that the outputs of the first and second label position measuring units 203a, 203b are the same in both cases of FIG. 5A and FIG. 5B. Thus, the threshold S403ef for detection of the liquid surface is the same in both cases of FIG. 5A and FIG. 5B. On the other hand, since the transmitted light intensity becomes lower when light passes through four layers of the labels, an error will arise when the same threshold is used to detect the liquid surface. The graph in the top right corner of FIG. 5C is an enlarged diagram of the transmitted light intensity profile. In the case of using the threshold S403ef, an error in detection position for liquid surface may occur between the case of FIG. 5A and the case of FIG. 5B. A filtered signal is used to reduce the error.

The liquid-surface position measurement device may include a filter section in which the transmitted light intensity profile is filtered to obtain a filtered waveform of the transmitted light intensity profile. The liquid-surface position measurement device uses the position of the feature point of the filtered waveform (e.g., the position of peak) to make correction for the liquid-surface position or the interface position of the sample.

The waveform shown in the lower portion of FIG. 5C is an example where the transmitted light intensity profile is passed through a filter with bandpass characteristics. Reference sign S501e denotes an example of filtering the transmitted light intensity profile in FIG. 5B, while reference sign S501f denotes an example of filtering the transmitted light intensity profile in FIG. 5A. Here, for the purpose of detecting a change in transmitted light intensity, preferable characteristics of a filter are bandpass characteristics that cut low frequencies and high frequencies for removing noise. Highpass characteristics may be employed for detection of a change of the liquid surface, if noise is low, for example.

The graph in the bottom right corner of FIG. 5C is an enlarged diagram of the bandpass filtered signal. The waveforms S501e, S501f of the bandpass filtered signal have peaks at the position where the transmitted light intensity changes at the liquid surface of the serum. The reason of this is considered that the change becomes maximum when the optical axis 207 of the light from the light source 201 exactly reaches the liquid surface position. The position where the change occurs hardly changes even when the attenuation is increased due to the label. Thus, the liquid-surface position measurement device is able to detect the liquid surface position with accuracy by detecting the peak of the filtered signal.

On the other hand, for the filtered signal, a similar peak is detected at the upper end of the label as well as the top surface of the serum. If only the filtered signal is used without comparison with the threshold to identify the liquid surface, it is difficult to identify the liquid surface position. Therefore, the liquid-surface position measurement device is configured to use the thresholds to locate a rough position of the liquid surface and then use the filtered signal for correction.

Possible specific methods for implementing a filter include, but are not limited to, the configuration using a FIR (Finate Impulse Response) filter to filter the digitized transmitted-light intensity profile and the digital filer configuration using an IIR (Infinate Impulse Response) filter, and a filter implemented by an analog circuit may be used.

In general, using high-pass filters provides sensitivity to high frequency noise because of extraction of high frequency components. The liquid-surface position measurement device in accordance with the embodiment measures the liquid surface even when a plurality of labels is affixed. Because of this, the optical measurement sensor is required to have high sensitivity, which thus is highly sensitive to noise. Therefore, the data of the filtered signal can be used for correction in order to be relatively less influenced by noise. Note that, if a peak of the filtered signal is not found in the vicinity of the position of the liquid surface temporarily detected using the threshold, the liquid-surface position measurement device may determine the values of the temporary liquid surface position as a final liquid-surface position.

More preferably, the transmitted light intensity may be represented in logarithmic scale such as a common logarithm, a natural logarithm, an absorbance or the like such that small signal change is highlighted. Then, the signal may pass through a filter such as a high-pass filter, a bandpass filter or the like such that a change at the liquid-surface position may be highlighted. Therefore, the liquid-surface position measurement device converts the transmitted light intensity profile to the logarithmic scale, and then inputs the converted profile to the filter section in order to acquire a filtered waveform. By doing this, a signal with a wide dynamic range from the case of no label being affixed to the case of a plurality of labels being affixed is able to be handled, enabling accurate detection of the liquid-surface position.

FIG. 6 is an operation flow for the liquid-surface position measurement device to measure the liquid-surface positon. The liquid-surface position measurement device uses the optical measurement sensor 202 to receive light from the light source 201, and measures a transmitted-light intensity profile in the longitudinal direction of the test tube 200 (S600). Subsequently, the liquid-surface position measurement device uses the label position measuring units 203a, 203b to measure a scattered-light intensity profile due to a label and measure the position of the label in the longitudinal direction (S601). For example, the liquid-surface position measurement device determines a position where a value of the scattered-light intensity profile becomes below a predetermined threshold, as a position where the label exists. Subsequently, the liquid-surface position measurement device generates a threshold at each position in the longitudinal direction of the test tube 200, depending on the label presence/absence from the outputs of the label position measuring units 203a, 203b (S602). The liquid-surface position measurement device performs comparison between the transmitted-light intensity profile and the threshold to calculate an intersection of them. The liquid-surface position measurement device detects the intersection as a liquid surface and determines the result as a temporary liquid-surface position (S603). Subsequently, the liquid-surface position measurement device calculates a signal resulting from filtering of the transmitted-light intensity profile measured at S600 (S604). Subsequently, the liquid-surface position measurement device searches the vicinity of the temporary liquid-surface position detected at S603 for the peak point of the filtered signal calculated at S604, and then determines the peak point as the liquid-surface position (S605).

Calculating the liquid-surface position through such a flow enables measurement of the liquid-surface position with accuracy and without false detection of liquid surface even if a plurality of labels is affixed.

It is noted that the order of the operation flow illustrated in FIG. 6 is not intended to be limiting. For example, in the order relationship between S600 and S601, it does not matter which step precedes, and both the measurements may be simultaneously performed. The measurements can be simultaneously performed by fixing the label position measuring units 203a, 203b, the light source 201 and the optical measurement sensor 202 and moving and scanning the test tube 200 in the vertical direction. For simultaneously obtaining the outputs of the label position measuring units 203a, 203b and the optical measurement sensor 202, the processing to shift the temporal waveform by a predetermined time period is performed to be adapted to the position in the longitudinal direction of the test tube 200.

Also, the processing may be performed in the following order: first searching for the peak point of the filtered signal calculated in S604, then storing a plurality of peak points in memory, and then, from these peak points, searching for the closest peak point to the temporary liquid surface. In either case, the liquid-surface position is capable of being measured with accuracy by using the transmitted-light intensity profile and the outputs of the label position measuring units 203a, 203b to find the liquid-surface position, and using a peak of the filtered signal in the vicinity of the found liquid-surface position to decide the liquid-surface position.

Figure 7:
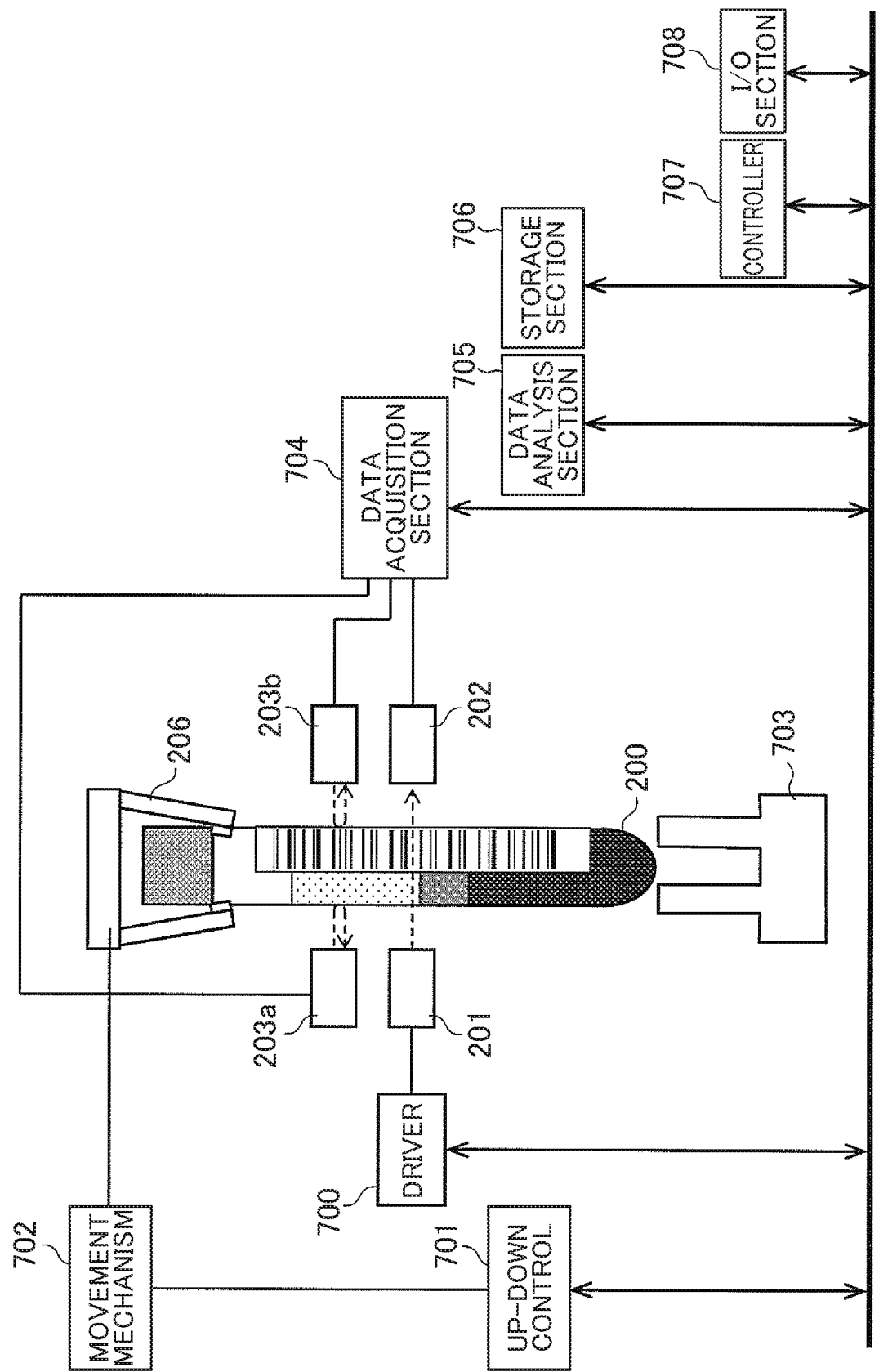
FIG. 7 is a diagram illustrating constituent components around the liquid-surface position measurement device in FIG. 2A and FIG. 2B.

FIG. 7 is a diagram illustrating constituent components around the liquid-surface position measurement device in FIG. 2A and FIG. 2B. The liquid-surface position measurement device includes not only the light source 201, the optical measurement sensor 202 and the label position measuring units 203a, 203b, but also a driver 700, an up-down control section 701, a movement mechanism 702, a test-tube grasping unit 206, a test-tube holder 703, a data acquisition section 704, a data analysis section 705, a storage section 706, a controller 707 and an input/output section 708.

The light source 201 emits light toward the test tube 200, and the optical measurement sensor 202 receives the light passing through the test tube 200. The label position measuring units 203a, 203b emits light to the test tube 200 and measures the light reflected or scattered by the test tube 200. The driver 700 drives the light source 201. The test tube 200 is placed on and transported by the test tube holder 703. The test-tube grasping unit 206 grips an upper portion of the test tube 200. The movement mechanism 702 moves the test-tube grasping unit 206 in the up-down directions in order to move the test tube 200 in the vertical direction. The movement mechanism 702 is controlled by the up-down control unit 701.

The data acquisition section 704 acquires outputs from the optical measurement sensor 202 and the label position measuring units 203a, 203b. The data acquisition section 704 temporarily stores the acquired data in the storage section 706. The data analysis section 705 acquires the data stored in the storage section 706 and analyzes the acquired data. The data analysis section 705 calculates the liquid-surface position or the interface position of the sample in the test tube 200, from the transmitted-light intensity profile in the longitudinal direction of the test tube 200 measured by the optical measurement sensor 202, and also from the label position in the longitudinal direction of the test tube 200 measured by the label position measuring units 203a, 203b. The analytical processing performed here is the processing (to generate a threshold, detect the temporary liquid surface, generate a filtered signal, and determine the final liquid surface) explained in S602 to S605 in FIG. 6. The data analysis section 705 temporarily stores the interface position or the liquid-surface position which is the analytical result, in the storage section 706. The input/output section 708 obtains and outputs data on the liquid-surface position from the storage section 706. The data is outputted to a higher-level controller and/or a display unit such as a display and/or the like. The controller 707 controls the sequence of operations.

Set values for a thresholds used for the interface position or the liquid-surface detection may be pre-stored in the storage section 706 via the input/output section 708. The threshold may be set for each kind of test tube, for each kind of label or for each device, and the input/output section 708 may be used to input each threshold and the thresholds may be stored in the storage section 706.

The data analysis section 705 can calculate the amount of liquid sample of interest from the calculated liquid-surface position. The data analysis section 705 can calculate the amount of liquid serum from information regarding the interface position between the serum and the separating agent, the top surface position of the serum, and physical dimensions such as a diameter of a test tube preset in the storage section 706 and/or the like. The amount of liquid serum thus calculated is output via the input/output section 708.

With such a configuration, while moving the test tube 200 in the vertical direction, the liquid-surface position measurement device measures the transmitted-light intensity profile and the output profiles of the label position measuring units 203*a*, 203*b*. The liquid-surface position measurement device then changes the thresholds based on the label presence/absence and calculates the liquid-surface position using the threshold. As a result, the interface position of the sample made up of a plurality of components is capable of detected with high accuracy even when a label is affixed to the test tube. In particular, even if the scattering and the attenuation of light is high in the test tube with a plurality of labels affixed thereto, the liquid-surface position is able to be detected with accuracy.

It is noted that the configuration in which the test tube 200 is moved in the vertical direction by the movement mechanism 702 has been in the embodiment, but is not intended to be limiting. The transmitted-light intensity profile and the label position in the longitudinal direction of the test tube 200 may be measured by securing the test tube 200 and moving the light source 201, the optical measurement sensor 202 and the label position measuring units 203*a*, 203*b*. Thus, the movement mechanism 702 may be configured to change the relative position in the vertical direction between the test tube 200 and each of the light source 201, the optical measurement sensor 202 and the label position measuring units 203*a*, 203*b*. While the relative position in the vertical direction is being changed using the movement mechanism 702, the optical measurement sensor 202 may measure the transmitted light passing from the light source 201, and the label position measuring units 203*a*, 203*b* may measure the position of the label(s).

The configuration of the label position measuring unit 203*a*, 203*b* having a light source and an optical measurement sensor has been described in the embodiment, but is not intended to be limiting. For example, an imaging means such as a CCD, a COMS camera or the like may be used to image the test tube 200 to identify the label position through image processing. Alternatively, while the test tube 200 is being rotated, a camera may be used to take a plurality of images of it and the images may be used to identify the presence/absence of a label on the optical axis for measurement of the transmitted-light intensity. By doing this, using a single camera enables identification of the presence/absence of the label on both sides of the intersection between the optical axis and the wall surface of the test tube 200.

Second Embodiment

Figure 8A:
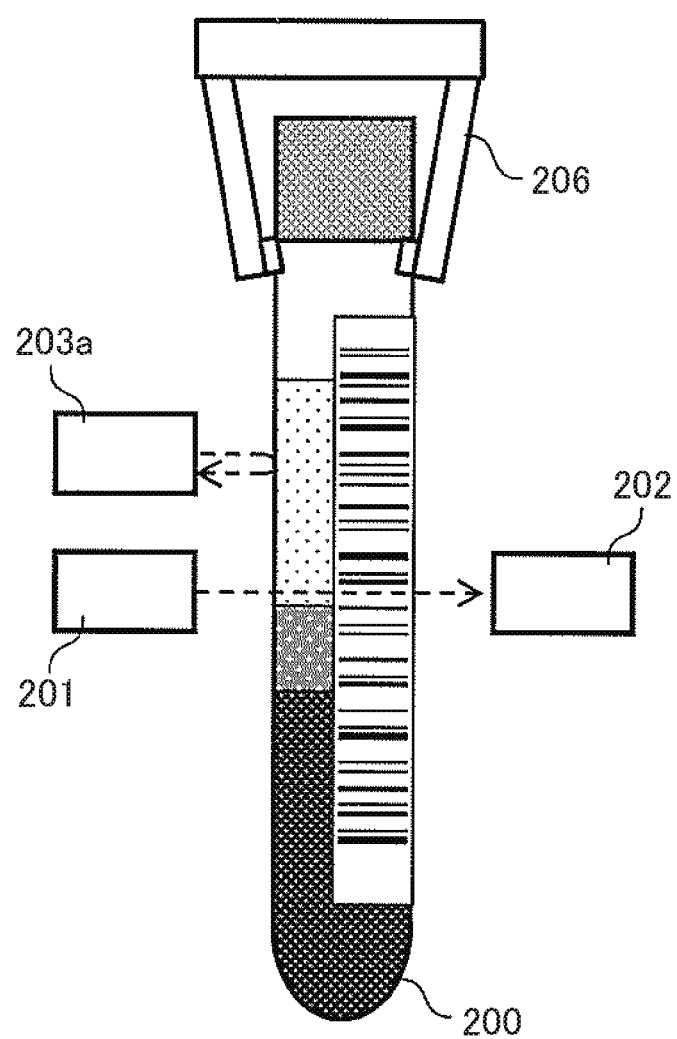
FIG. 8A is a side view of a liquid-surface position measurement device in accordance with a second embodiment.
Figure 8B:
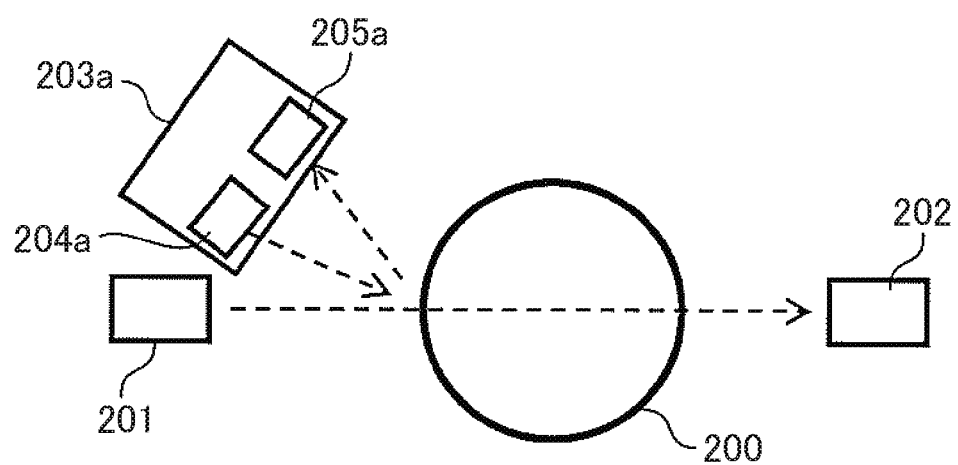
FIG. 8B is a top view of the liquid-surface position measurement device in accordance with the second embodiment.

FIG. 8A and FIG. 8B are configuration diagrams of a liquid-surface position measurement device in accordance with a second embodiment. The liquid-surface position measurement device includes the light source 201, the optical measurement sensor 202 and the label position measuring unit 203*a*. The configuration described in the first embodiment includes the two label position measuring units, but the effects of detecting the liquid surface with high accuracy are produced even when the single label position measuring unit 203*a* is used.

FIG. 9A is a first example of the transmitted-light intensity profile measured by the liquid-surface position measurement device, the output from the label position measuring unit, and the thresholds, in accordance with the embodiment. As illustrated in FIG. 9A, where a label is not affixed to the test tube, the output of the label position measuring unit 203*a* is Hi level, and thus a label is not detected. Therefore, the liquid-surface position measurement device makes a comparison between a threshold S903*a* for the case of no label existing and a transmitted-light intensity profile S902*a* to detect the liquid-surface position.

FIG. 9B is a second example of the transmitted-light intensity profile measured by the liquid-surface position measurement device, the output from the label position measuring unit, and the thresholds, in accordance with the embodiment. As illustrated in FIG. 9B, where a label is affixed to only one side of the test tube and the label is located on the side of the label position measuring unit 203*a*, the output of the label position measuring unit 203*a* is Lo level within the label range, and thus the label is detected. The liquid-surface position measurement device sets a lower threshold S903*b* (as compared with where no label exists) in the range where the label is detected. The liquid-surface position measurement device makes a comparison between the threshold S903*b* and a transmitted-light intensity profile S902*b* to detect the liquid-surface position.

Figure 9C:
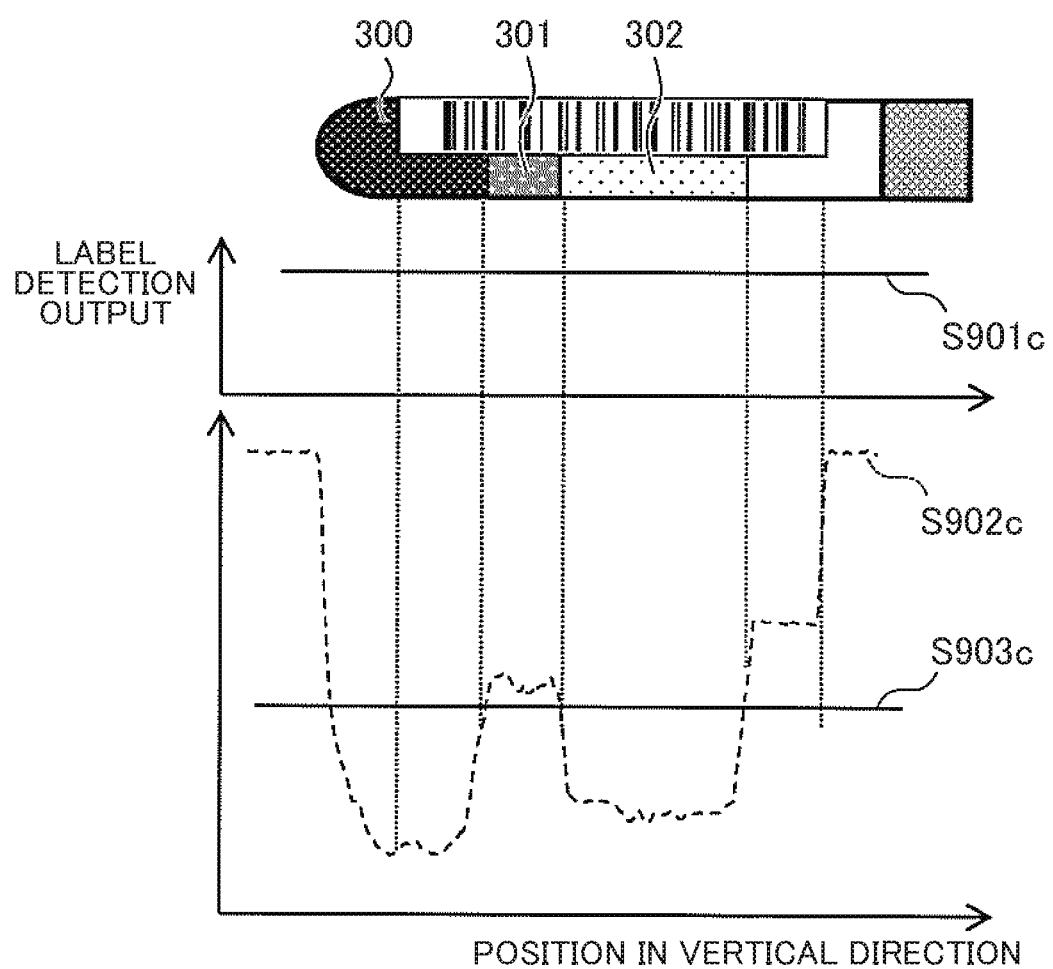
FIG. 9C is a third example of a transmitted-light intensity profile measured by the liquid-surface position measurement device, output from a label position measuring unit, and thresholds, in accordance with the second embodiment.

FIG. 9C is a third example of the transmitted-light intensity profile measured by the liquid-surface position measurement device, the output from the label position measuring unit, and the thresholds, in accordance with the embodiment. As illustrated in FIG. 9C, where a label is affixed to only one side of the test tube and the label is located on the opposite side from the label position measuring unit 203*a*, the output of the label position measuring unit 203*a* is Hi level, and thus a label is not detected. Therefore, the liquid-surface position measurement device makes a comparison between a threshold S903*c* for the case of no label existing and a transmitted-light intensity profile S902*c*. Even in this state, the liquid surface is detected. Because of this, the threshold S903*c* for the case of no label existing is set at a value that allows the liquid-surface position to be measured in both the states illustrated in FIG. 9A and FIG. 9C. In other words, in both the states in FIG. 9A and FIG. 9C, the threshold S903*c* may be set at a value that can give an intersection with the transmitted-light intensity profile in the liquid-surface position.

Figure 9D:
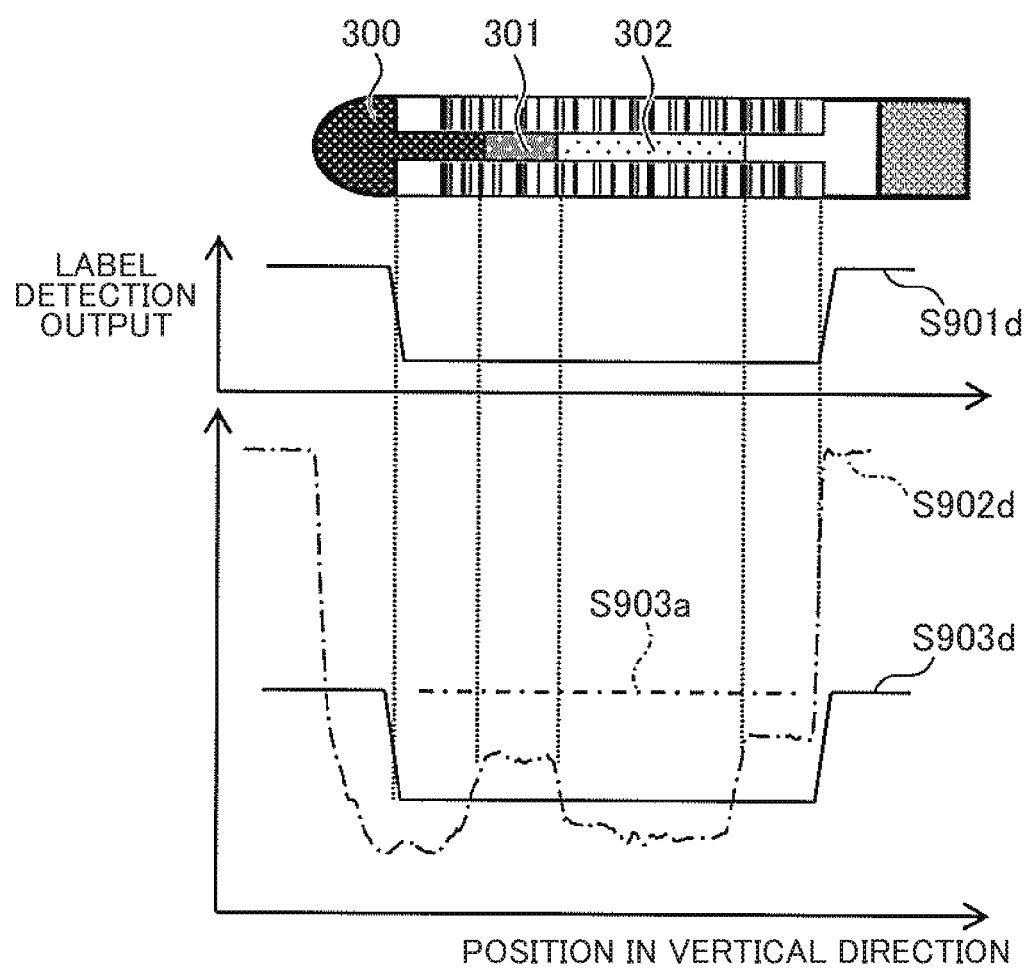
FIG. 9D is a fourth example of a transmitted-light intensity profile measured by the liquid-surface position measurement device, output from a label position measuring unit, and thresholds, in accordance with the second embodiment.

FIG. 9D is a fourth example of the transmitted-light intensity profile measured by the liquid-surface position measurement device, the output from the label position measuring unit, and the thresholds, in accordance with the embodiment. As illustrated in FIG. 9D, where a label(s) is affixed to both sides, the output of the label position measuring unit 203a is Lo level within the label range, and thus a label is detected. The liquid-surface position measurement device sets a lower threshold S903d (as compared with where no label exists) in the range where the label is detected. In this example, because the label is affixed to both sides, the transmitted-light intensity is lower than that in FIG. 9B. Therefore, the threshold S903d for the range where the label exists may be set to fall within a range in which the liquid surface can be detected even where the label is affixed on one side and where the label is affixed on both sides.

By setting the threshold as described above, even in the use of only one label position measuring unit, the detection of the liquid-surface position is enabled. In the embodiment, as compared with the use of two label position measuring units, setting the threshold is severe. However, the threshold is changed by the output of the label position measuring unit 203a, whereby the liquid surface position can be measured. Note that the label position measuring position 203a may be located on the side of either the light source 201 or the optical measurement sensor 202.

Third Embodiment

Figure 10A:
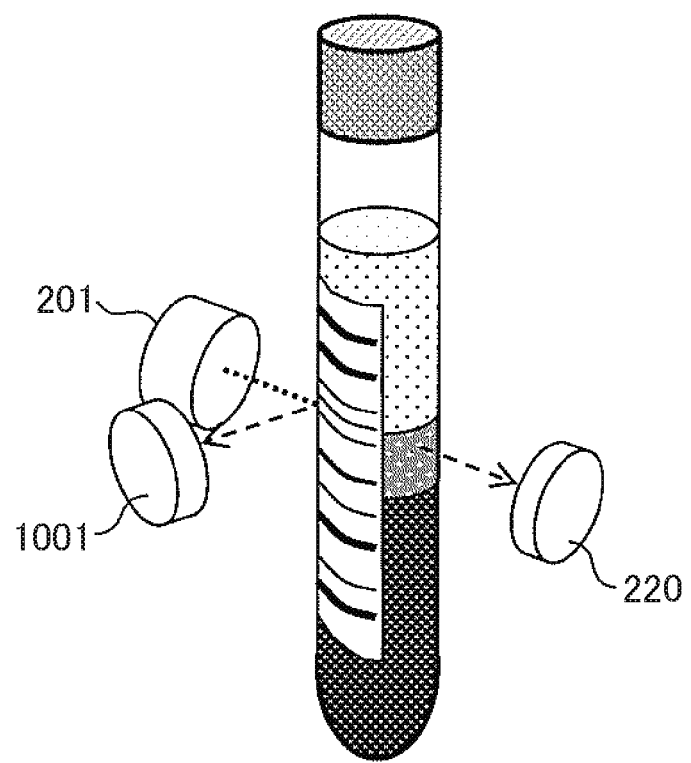
FIG. 10A is a side view of a liquid-surface position measurement device in accordance with a third embodiment.
Figure 10B:
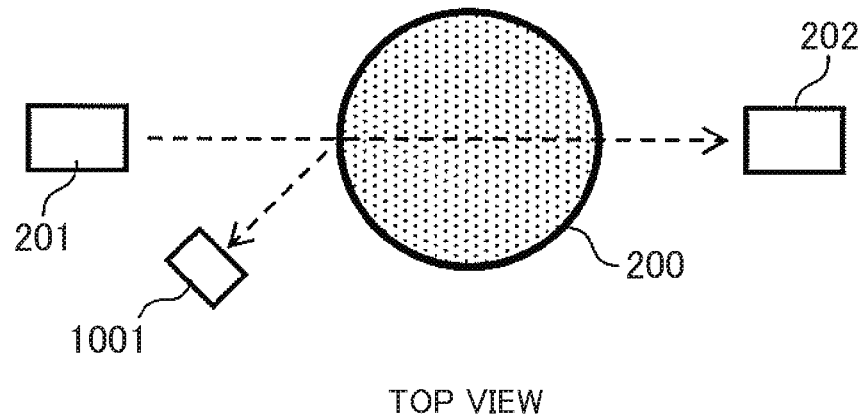
FIG. 10B is a top view of the liquid-surface position measurement device in accordance with the third embodiment.

FIG. 10A and FIG. 10B are configuration diagrams of a liquid-surface position measurement device in accordance with the embodiment. The liquid-surface position measurement device includes the light source 201, the optical measurement sensor 202 and an optical measurement sensor 1001. In the embodiment, the label position measuring unit 203a described in the first and second embodiments is configured to have a light source shared with the light source 201 used for measurement of the transmitted-light intensity.

The light emanating from the light source 201 passes through the test tube 200, which is then received by the optical measurement sensor 202. Also, a portion of the light from the light source 201 is scattered or reflected by the surface of the test tube 200, and the portion is received by the optical measurement sensor 1001. The amount of light received by the optical measurement sensor 1001 is influenced by the state of the surface of the test tube 200, or the label presence/absence. Accordingly, the liquid-surface position measurement device is able to detect the label presence/absence from the output of the optical measurement sensor 1001. The liquid-surface position measurement device detects the label presence/absence and changes the threshold depending on the label presence/absence to measure the liquid surface.

According to the embodiment, the influence of the label can be reduced, so that the liquid surface can be calculated with high accuracy. Further, the number of constituent components of the device can be decreased by making the light source shareable between the measurement of the transmitted-light intensity and the detection of a label.

The present invention is not limited to the embodiments described above and encompasses numerous modifications. The above embodiments have been described in detail for the purpose of explaining the present invention clearly, and the present invention is not necessarily limited to including all the configurations described above. Further, a portion of the configuration of one embodiment may be substituted by the configuration of another embodiment. Further, the configuration of one embodiment may be added to the configuration of another embodiment. Further, for a portion of the configuration of each embodiment, another configuration may be added thereto, removed therefrom or substituted therefor.

Each of the configurations, each of the functions (e.g., analytical processing) and/or the like may be implemented by software by causing a processor to interpret and execute a program for implementing the individual function. Information regarding programs, files and/or the like which implement each function may be stored in a storage device such as memory, hard disks, SSD (Solid State Drive) and/or the like, or on a storage medium such as IC cards, SD cards, DVDs and/or the like. Further, each of the configurations and the like described above may be implemented wholly or partly in hardware by, for example, designing of an integrated circuit and/or the like.

Only the control lines and information lines considered necessary in terms of explanation are illustrated in the above embodiments, and all the control lines and all the information lines in products are not necessarily shown. All the configurations may be mutually connected.

LIST OF REFERENCE SIGNS

100 . . . Preprocessing system
101 . . . Transport line
102 . . . Load module
103 . . . Centrifugal separation module
104 . . . Sample check module
105 . . . Unplug module
106 . . . Labeler
107 . . . Aliquot module
108 . . . Plug module
109 . . . Classification module
110 . . . Storage module
111 . . . Control PC
112 . . . Automatic analyzer
120 . . . Biological sample analysis device
200 . . . Test tube
201 . . . Light source
202 . . . Optical measurement sensor
203 . . . Label position measuring unit
204 . . . Light source
205 . . . Optical measurement sensor
206 . . . Test-tube grasping unit
207 . . . Optical axis
300 . . . Clot
301 . . . Separating agent
302 . . . Serum
700 . . . Driver
701 . . . Up-down control section
702 . . . Movement mechanism
703 . . . Test-tube holder
704 . . . Data acquisition section
705 . . . Data analysis section
706 . . . Storage section
707 . . . Controller
708 . . . Input/output section
1001 . . . Optical measurement sensor

The invention claimed is:
1. A sample liquid-surface position measurement device, comprising:
a first light source that illuminates a side face of a container containing a sample;
a first optical measurement sensor that is located on the opposite side of the container from the first light source, and measures transmitted light from the first light source;
a first label position measuring unit that measures a position of a label affixed to the container; and an analysis section that calculates a liquid-surface position or an interface position of the sample in the container, from transmitted-light intensity data in a longitudinal direction of the container which is measured by the first optical measurement sensor, and from the position of the label in the longitudinal direction of the container which is measured by the first label position measuring unit, wherein the first label position measuring unit includes a second light source that illuminates a side face of the container, and a second optical measurement sensor that measures scattered light or reflected light resulting from impinging of light from the second light source on the container, and the second light source emits light to an intersection between an optical axis of the light from the first light source and the surface of the container.

2. The sample liquid-surface position measurement device according to claim 1, wherein the second light source illuminates the container at an inclination of from 5 degrees to 40 degrees with respect to an optical axis of the light from the first light source.

3. The sample liquid-surface position measurement device according to claim 1, further comprising a second label position measuring unit that measures a position of a label affixed to the container, wherein the first label position measuring unit is placed on the side of the first light source and measures a position of the label in a position where the light from the first light source enters the container, and the second label position measuring unit is placed on the side of the first optical measurement sensor and measures a position of the label in a position where the light from the first light source passes through and emerges from the container.

4. The sample liquid-surface position measurement device according to claim 1, wherein the analysis section reduces a threshold within a range where the label is affixed, and makes a comparison between the threshold and the transmitted-light intensity data in order to calculate a liquid-surface position or an interface position of the sample.

5. The sample liquid-surface position measurement device according to claim 1, wherein the sample includes serum obtained after centrifugation of blood, and the liquid-surface position or the interface position includes at least one of an interface between blood clot and a separating agent, an interface between the serum and the separating agent, and a top liquid surface of the serum.

6. The sample liquid-surface position measurement device according to claim 5, wherein the analysis section calculates the amount of liquid of the serum from the liquid-surface position or the interface position.

7. The sample liquid-surface position measurement device according to claim 5, wherein the light of the first light source has a wavelength selected from the range of from 1400 nm to 1600 nm.

8. The sample liquid-surface position measurement device according to claim 1, wherein the analysis section includes a filter section that filters the transmitted-light intensity data to obtain a filtered waveform of the transmitted-light intensity data, and the analysis section uses a position of a feature point of the filtered waveform to make correction for the liquid-surface position or the interface position of the sample.

9. The sample liquid-surface position measurement device according to claim 8, wherein the analysis section converts the transmitted-light intensity data to logarithmic scale, and then inputs the converted transmitted-light intensity data to the filter section in order to acquire the filtered waveform.

10. The sample liquid-surface position measurement device according to claim 1, further comprising a movement mechanism, wherein while the movement mechanism is used to change a relative position in the vertical direction between the container, the first light source, the first optical measurement sensor, and the first label position measuring unit, the first optical measurement sensor measures transmitted light passing from the first light source, and the first label position measuring unit measures a position of the label.

11. The sample liquid-surface position measurement device according to claim 1, wherein the first label position measuring unit includes a second optical measurement sensor that measures scattered light or reflected light resulting from impinging of light from the first light source on the container to measure a position of a label affixed to the container, and the second light source is shared with the first light source.

12. A biological sample analysis device comprising:

a preprocessing unit including the sample liquid-surface position measurement device according to claim 1, and an automatic analyzer that analyzes components of the sample.

13. A sample liquid-surface position measurement method, comprising:

causing a first light source to illuminate a side face of a container containing a sample;

causing a first optical measurement sensor, which is placed on the opposite side of the first light source with the container therebetween, to measure transmitted light from the first light source;

causing a first label position measuring unit to measure a position of a label affixed to the container; and causing an analysis section to calculate a liquid-surface position or an interface position of the sample in the container, based on transmitted-light intensity data in a longitudinal direction of the container which is measured by the first optical measurement sensor, and the position of the label in the longitudinal direction of the container which is measured by the first label position measuring unit, wherein the first label position measuring unit includes:

a second light source that illuminates a side face of the container; and a second optical measurement sensor that measures either light scattered or light reflected by impinging of light from the second light source on the container, and the second light source emits light to an intersection between an optical axis of the light from the first light source and the surface of the container.

* * * * *